United States Patent [19]

Ackermann et al.

[11] Patent Number: 5,559,232

[45] Date of Patent: Sep. 24, 1996

[54] CARBOXAMIDES

[75] Inventors: Jean Ackermann; David Banner, both of Basel, Switzerland; Klaus Gubernator, Freiburg, Germany; Kurt Hilpert, Hofstetten; Gérard Schmid, Kienberg, both of Switzerland

[73] Assignee: Hoffmann-La Roche Inc., Nutley, N.J.

[21] Appl. No.: 300,821

[22] Filed: Sep. 2, 1994

[30]     Foreign Application Priority Data

Sep. 7, 1993 [CH] Switzerland ............... 2667/93
Jul. 5, 1994 [CH] Switzerland ............... 2150/94

[51] Int. Cl.$^6$ ............. C07D 211/14; C07D 265/28; C07D 401/12; C07D 413/12
[52] U.S. Cl. ............ 544/121; 544/162; 544/360; 546/231
[58] Field of Search ............ 546/231; 544/121 A, 544/162, 360

[56]            References Cited

U.S. PATENT DOCUMENTS

| | | |
|---|---|---|
| 4,227,006 | 10/1980 | Okamoto et al. . |
| 4,258,192 | 3/1981 | Okamoto et al. . |
| 4,879,313 | 11/1989 | Tjoeng et al. . |
| 5,037,808 | 8/1991 | Tjoeng et al. . |
| 5,053,393 | 10/1991 | Tjoeng et al. . |
| 5,260,307 | 11/1993 | Ackerman et al. . |
| 5,405,854 | 4/1995 | Ackermann ............... 514/315 |

FOREIGN PATENT DOCUMENTS

| | | |
|---|---|---|
| 9179490 | 7/1991 | Australia . |
| 0097630 | 1/1984 | European Pat. Off. . |
| 0381033 | 8/1990 | European Pat. Off. . |
| 468231 | 7/1991 | European Pat. Off. . |
| 0462960 | 12/1991 | European Pat. Off. . |
| 0502536 | 3/1992 | European Pat. Off. . |
| 2506306 | 11/1982 | France . |

OTHER PUBLICATIONS

J.Med.Chem. 33, 1990, 1406–1413.
BiochemJ. 55, 1955, 170–171.
J.Heterocycl. Chem. 23, 1986, 929–933.
J.Med.Chem. 1980, 23, 1293–1299, Vol. 12.
Pharmazie 39, 1984, 226–230.
Thrombosis & Haemotasis 67, 1992, 56–59.
Drugs of the Future 17, 1992, 1087–90.

*Primary Examiner*—Robert Gerstl
*Attorney, Agent, or Firm*—George M. Gould; William H. Epstein; Bruce A. Pokras

[57]            ABSTRACT

The novel carboxamides of the formula

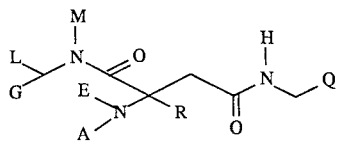

wherein A, E, G, L, M, R and Q have the significance given in the description, as well as hydrates or solvates thereof inhibit thrombin-induced platelet aggregation and fibrinogen coagulation in plasma. They can be manufactured starting from the corresponding acid and the corresponding amine $H_2NCH_2Q$.

74 Claims, No Drawings

CARBOXAMIDES

SUMMARY OF THE INVENTION

The invention is concerned with novel carboxamides of the formula

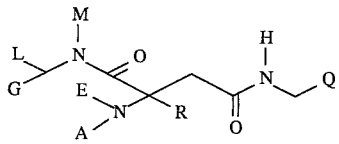

wherein

E is hydrogen,

G is H, lower-alkyl or (optionally bonded via lower-alkylene) COOH, COO-lower-alkyl, lower-alkonyl, OH, lower-alkanoyloxy, lower-alkoxy, aryl-lower-alkoxy, $CONH_2$, $CONHCH_2CH_2OH$, CONHOH, $CONHOCH_3$, CONHO-benzyl, $CONHSO_2$-lower-alkyl, $CONHCH_2CH_2$-aryl, CONH-cycloalkyl, $CONHCH_2$-heteroaryl, $NH_2$, NHCOO-lower-alkyl, NHCOO-lower-aralkyl, $NHSO_3H$, ($NHSO_2$ or $NHSO_3$)-lower-alkyl, NH lower-alkanoyl, NHCOCOOH, NHCOCOO-lower-alkyl, NH-cycloalkyl, NH-(3,4-dioxo-2-hydroxy-cyclobut-1-enyl), NH-[2-lower-(alkoxy or -alkenyloxy)-3,4-dioxocyclobut-1-enyl], $NHCH_2$-heteroaryl, NHCOCO-(aryl or lower-alkyl), $NHCOCH_2Cl$, NHCO-lower-alkylene-O-(lower-alkyl or aryl), $NHCOCH_2$[aryl, heteroaryl or —N(Het)], NHCOC(NOH)-lower-alkylene-COOH, $NHSO_2$—N(Het), NHCO-(aryl, heteroaryl or heterocyclyl), $NHPO_3(R^{10},R^{20})$, heteroaryl or a group CO-N(Het), $R^{10}$ and $R^{20}$ are H, lower-alkyl or phenyl, M is H, lower-alkyl or-alkenyl, aryl, heteroaryl, cycloalkyl or (aryl, heteroaryl or cycloalkyl)-lower-alkyl and L is H, lower-alkyl, aryl, cycloalkyl or (aryl or cycloalkyl)-lower-alkyl or M and L together with the atoms to which they are attached form a group —N(Het) or E and G together form a methylene or carbonyl group and M is H, lower-alkyl or -alkenyl, aryl, heteroaryl, cycloalkyl, (aryl, heteroaryl or cycloalkyl)-lower-alkyl or carboxy-lower-alkyl and L is H, lower-alkyl, aryl, cycloalkyl or (aryl or cycloalkyl)-lower-alkyl, A is H, alkyl, lower-aralkyl or a group of the formula:

—C(O)R²      (A¹),

—S(O)₂N(R³,R⁴)      (A²)

or, where group Q contains a hydroxy group and/or where E and G together are $CH_2$ or CO, then A can also be a group of the formula

—S(O)₂R⁵      (A³)

or, where E and G together are $CH_2$ or CO,

A can also be a group of the formula:

—S(O)₂R⁵      (A³), $R^2$ is lower-alkyl, aryl, heteroaryl or cycloalkyl optionally bonded via lower-alkylene, carbo-lower-alkoxy bonded via lower-alkylene or —(O or S)—(aryl, heteroaryl or cycloalkyl) bonded via lower-alkylene, whereby a lower-alkylene group present in $R^2$ can be substituted by hydroxy, amino or lower-alkanoylamino in the α-position to the carbonyl group to which $R^2$ is bonded or $R^2$ is halogen, carboxy, lower alkoxy, amino, mono- or di-lower-alkyl-amino or a group —N(Het) bonded via lower alkylene or $R^2$ is a group —$OR^{22}$ or —$NHR^{22}$, $R^{22}$ is lower-alkyl, aryl, heteroaryl or cycloalkyl optionally bonded via lower-alkylene or lower-aralkyl substituted in the lower-alkyl moiety by aryl, carbo-lower-alkoxy or COOH, $R^3$ and $R^4$ each independently are hydrogen, alkyl or aryl-lower-alkyl or together with the N atom to which they are attached form a group —N(Het), $R^5$ is aryl, heteroaryl, heterocyclyl, alkyl or cycloalkyl, —N(Het) is N-bonded —$N(CH_2)_{4-9}$ optionally interrupted by O, S, NH or N-lower-alkyl and optionally substituted by up to 2 substituents from the group of lower-alkyl, OH, oxo, COOH, COO-lower-alkyl, $CH_2OH$ and $CH_2O$-benzyl, Q is a group of formula $Q^1$ or $Q^2$:

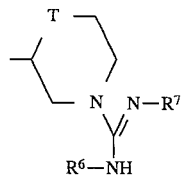

(Q¹)

and

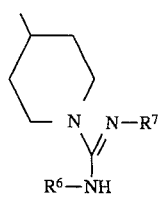

(Q²)

T is $CH_2$ or O one of $R^6$ and $R^7$ is hydrogen or carbo-lower-alkoxy and the other is hydrogen, carbo-lower-alkoxy or hydroxy, and R is hydrogen or lower-alkyl, as well as hydrates or solvates and physiologically compatible salts thereof.

DETAILED DESCRIPTION

In accordance with this invention, any conventional pharmaceutically acceptable salt of the compound of formula I can be utilized. Examples of pharmaceutically acceptable salts of the compounds of formula I are salts with mineral acids such as hydrochloric acid, sulphuric acid, sulphurous acid or phosphoric acid; or with organic acids such as methanesulphonic acid, p-toluenesulphonic acid, acetic acid, trifluoroacetic acid, citric acid, fumaric acid, maleic acid, tartaric acid, succinic acid or salicylic acid. The compounds of formula I which have a free carboxy group can also form pharmaceuticallly acceptable basic salts with bases. Among these basic salts are alkali metal, alkaline earth metal, ammonium and alkylammonium salts such as the Na, K, Ca or tetramethylammonium salts are examples of such salts. The compounds of formula I can also be present in the form of zwitterions.

The compounds of formula I can be solvated, especially hydrated. The hydration can be effected in the course of the manufacturing process or can occur gradually as a consequence of hygroscopic properties of an initially anhydrous compound of formula I.

The compounds of formula I contain at least two asymmetric C atoms and can therefore be present as a mixture of diastereomers or as the optically pure compound.

In the scope of the invention the term "lower" denotes groups which contain 1 to 6, preferably 1 to 4, C atoms. Thus, lower-alkyl, alone or in combination, denotes straight or branched groups containing 1 to 6, preferably 1 to 4, C atoms such as methyl, ethyl, propyl, isopropyl, butyl, t-butyl, 2-butyl and pentyl. Lower-alkyl groups are preferred as alkyl groups. Lower alkylene denotes alkylene groups containing from 1 to 6 carbon atoms with methylene being an example of lower-alkylene.

When alkyl, alkylene, alkoxy are utilized, the preferred alkyl, alkkylene or alkoxy groups are lower alkyl, lower alkylene or lower alkoxy groups containing from 1 to 6 carbon atoms.

Aryl denotes groups such as phenyl and 1- or 2-naphthyl optionally having one or more substituents such as halogen, e.g. chlorine, or lower-alkyl or alkoxy, e.g. $CH_3$, t-butyl, OH, $OCH_3$, phenyl, $CF_3$, $OCF_3$, cyclopentyl, CN, COOH, $COOCH_3$, $COOC_2H_5$, $CONH_2$ or tetrazolyl. When aryl us substituted, it generally has from 1 to 2 substituents.

Heteroaryl groups are aromatic substituents with a ring system containing from 5 to 10 atoms in the ring system. This ring system preferably contains one or two rings formed from carbon atoms with one or more heteroatoms such as N or O atoms in the ring system. Generally it is preferred that the heteroaryl group contain one through 3 hetero atoms. Examples thereof are 2-, 3- or 4-pyridyl, also in the form of their N-oxides, furyl, pyrimidinyl, indolyl, pyrazinyl, pyridazinyl, tetrazolyl, oxadiazolyl, quinolyl or imidazolyl. Generally these ring systems contain from 1 to 3 hetero atoms which can be nitrogen or oxygen. The ring systems can be substituted, e.g. by oxo, lower-alkyl such as $CH_3$, halogen such as chlorine, or amino.

Cycloalkyl groups contain 3 to 8 C atoms. Cyclopropyl, cyclopentyl and cyclohexyl are examples of these.

Heterocyclyl denotes 5- to 10-membered non-aromatic, partially or completely saturated ring system, such as tetrahydroquinolyl or tetrahydropyridazinyl, which contain one or two rings in the system and at least one hetero atom in the ring system, preferably one or two N and/or O atoms. This ring system can be optionally substituted with one or more substituents such as lower-alkyl, e.g. methyl.

N[Het] as used herein designates a substituent with a heterocyclic ring structure with at least one nitrogen in the ring through which the substituent is attached. Among the preferred N[Het] are monosaturated 5- to 10-membered ring structure containing from 4 to 9 carbon atoms and one nitrogen atom with at most two other hetero atoms selected from the group consisting of nitrogen or oxygen. This heterocyclic ring structure can be unsubstituted or substituted in at least two places on the ring with a substituent selected from the group consisting of lower alkyl, —COOH, —COO-lower alkyl, —CH$_2$OH, or —CH$_2$O-benzyl.

Examples of N(Het) are hexahydroazepino, morpholino and methylpiperazinyl.

Examples of compounds in accordance with the invention are those of the formula

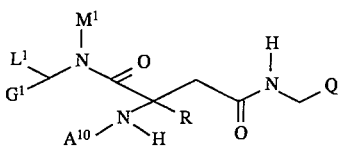

Ia wherein $G^1$ is H, lower-alkyl or (optionally bonded via lower-alkylene) COOH, COO-lower-alkyl, lower-alkanoyl, OH, lower-alkanoyloxy, lower-alkoxy, aryl-lower-alkoxy, $CONH_2$, $CONHCH_2CH_2OH$, CONHOH, $CONHOCH_3$, CONHO-benzyl, $CONHSO_2$-lower-alkyl, $CONHCH_2CH_2$-aryl, CONH-cycloalkyl, CON-$HCH_2$-heteroaryl, $NH_2$, NHCOO-lower-alkyl, NHCOO-lower-aralkyl, $NHSO_3H$, ($NHSO_2$ or $NHSO_3$)-lower-alkyl, NH-lower-alkanoyl, NHCO-COOH, NHCOCOO-lower-alkyl, NH-cycloalkyl, NH-(3,4-dioxo-2-hydroxycyclobut-1-enyl), NH-[2-lower-(alkoxy or -alkenyloxy)-3,4-dioxocyclobut-1-enyl], $NHCH_2$-heteroaryl, NHCOCO-(aryl or lower-alkyl), $NHCOCH_2Cl$, NHCO-lower-alkylene-O-(lower-alkyl or aryl), $NHCOCH_2$[aryl, heteroaryl or —N(Het)], NHOOC(NOH)-lower-alkylene-COOH, $NHSO_2$—N(Het), NHCO-(aryl, heteroaryl or heterocyclyl), $NHPO_3(R^{10},R^{20})$, heteroaryl or a group CO—N(Het), $R^{10}$ and $R^{20}$ are H, lower-alkyl or phenyl, $M^1$ is H, lower-alkyl or -alkenyl, aryl, heteroaryl, cycloalkyl or (aryl, heteroaryl or cycloalkyl)-lower-alkyl and $L^1$ is H, lower-alkyl, aryl, cycloalkyl or (aryl or cycloalkyl)-lower-alkyl or $M^1$ and $L^1$ together with the atoms to which they are attached form a group —N(Het), $A^{10}$ is H, alkyl, lower-aralkyl or a group of the formula:

  (A$^1$),

  (A$^2$)

or, where group Q contains a hydroxy group, then $A^{10}$ can also be a group of the formula

  (A$^3$), and

R, $R^2$ to $R^5$, —N(Het) and Q have the above significance.

Further examples of compounds in accordance with the invention are those of the formula

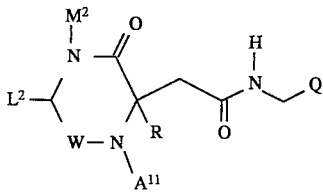

Ib wherein

W is methylene or carbonyl, $M^2$ is H, lower-alkyl or -alkenyl, aryl, heteroaryl, cycloalkyl, (aryl, heteroaryl or cycloalkyl)-lower-alkyl, or carboxy-lower-alkyl, $L^2$ is H, lower-alkyl, aryl, cycloalkyl or (aryl or cycloalkyl)-lower-alkyl and $A^{11}$ is H, alkyl, lower-aralkyl or a group of the formula:

—C(O)R² (A¹),

—S(O)₂N(R³,R⁴) (A²)

or

—S(O)₂R⁵ (A³)

and

R, R² to R⁵ and Q have the above significance.

Among the compounds Ia there are preferred those in which L¹ is hydrogen and G¹ is COOH, COO-lower-alkyl, NHCOO-lower-aralkyl or NHCO(aryl or heteroaryl) optionally bonded via lower-alkylene, further those in which M¹ is lower-alkyl or cycloalkyl and/or in which A¹⁰ is a group of the formula

—C(O)—R² (A¹)

in which R² is a group R²², —OR²² or —NHR²² and R²² is lower-alkyl or aryl, heteroaryl or cycloalkyl optionally bonded via lower-alkylene or in which R² is carbo-lower-alkoxy bonded via lower-alkylene or —(O or S)-(aryl or heteroaryl) bonded via lower-alkylene, whereby a lower-alkylene group present in R² can be substituted by OH or lower-alkanoylamino in the α-position to the carbonyl group to which R² is bonded.

Further preferred compounds Ia are those in which A¹⁰ is a group —S(O)₂aryl and Q contains a group OH or in which A¹⁰ is morpholinosulphonyl.

Among the compounds of formula Ia there are further preferred those in which L¹ is hydrogen and G¹ is (optionally bonded via lower alkylene) NHCO-lower-alkylene-O-(lower-alkyl or aryl), NHCOCH₂[aryl, heteroaryl or —N(Het)], NHCOC(NOH)-lower-alkylene-COOH, NHSO₂-N(Het), NHCO-heterocyclyl or CON(CH₂)₄₋₉ optionally interrupted by O or S and optionally substituted by up to 2 substituents from the group of lower-alkyl, COOH, COO-lower-alkyl, CH₂OH and CH₂O-benzyl, and further those in which A¹⁰ is H, lower-alkyl, lower-aralkyl or a group

—C(O)—R² (A¹)

in which R² is halogen, carboxy, lower-alkoxy, amino, or mono- or di-lower-alkyl-amino bonded via lower-alkylene or a group —N(Het) bonded via lower-alkylene or R² is a group —NHR²² in which R²² is a lower-aralkyl group substituted in the lower-alkyl moiety by aryl, carbo-lower-alkoxy or COOH.

Among the particularly preferred compounds are those which have the formula

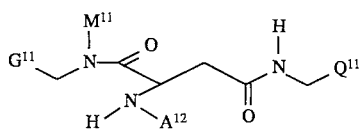

Ia1 wherein

G¹¹ is a group COOH, COO-lower-alkyl or NHCO-heteroaryl, which group is optionally bonded via lower-alkylene, M¹¹ is lower-alkyl or cycloalkyl, A¹² is lower-aralkyl or a group —C(O)R²¹, —S(O)₂-aryl or —S(O)₂-N(Het)", R²¹ is a group —S-heteroaryl or —N(Het)", which group is bonded via lower-alkylene, or R²¹ is lower-aralkoxy or lower-alkyl, —N(Het)" is N-bonded —N(CH₂)₄₋₉ optionally interrupted by O, S, NH or N-lower-alkyl, Q¹¹ is a group of formula

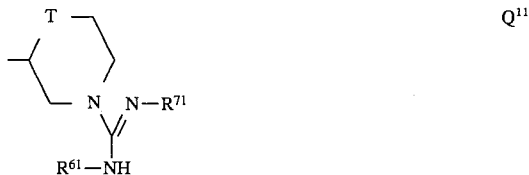

Q¹¹

T is CH₂ or O, one of R⁶¹ and R⁷¹ is H and the other is H or OH, and physiologically compatible salts thereof, as well as those compounds of the above formula Ib, wherein W is carbonyl, M² is cycloalkyl, L² is H, A¹¹ is —S(O)₂-aryl, R is H and Q is a group of formula Q¹ wherein T is CH₂, and each R⁶ and R⁷ are H.

The following are examples of compounds of formula Ia:

Ethyl [[(S)-3-[(S)-1-(amino-imino-methyl)-piperidin-3-yl-methylcarbamoyl]-2-benzyloxycarbonylamino-propionyl]-cyclopropyl-amino]acetate, ethyl 3-[[(S)-3-[(S)-1-(amino-imino-methyl)-piperidin-3-ylmethylcarbamoyl]-2-benzyloxycarbonylamino-propionyl]-cyclopropyl-amino]-propionate, ethyl [[(S)-3-[(S)-1-(amino-imino-methyl)-piperidin-3-ylmethylcarbamoyl]-2-benzyloxycarbonylamino-propionyl]-butylamino]-acetate, ethyl 3-[[(S)-3-[(S)-1-(amino-imino-methyl)-piperidin-3-ylmethylcarbamoyl]-2-benzyloxycarbonylamino-propionyl]-butylamino]-propionate,

[[(S)-3-[(S)-1-(amino-imino-methyl)-piperidin-3-ylmethylcarbamoyl]-2-benzyloxycarbonylamino-propionyl]-cyclopropyl-amino]acetic acid, 3-[[(S)-3-[(S)-1-(amino-imino-methyl)-piperidin-3-ylmethylcarbamoyl]-2-benzyloxycarbonylamino-propionyl]-cyclopropyl-amino]propionic acid,

[[(S)-3-[(S)-1-(amino-imino-methyl)-piperidin-3-ylmethylcarbamoyl]-2-benzyloxycarbonylamino-propionyl]-butyl-amino]-acetic acid, 3-[[(S)-3-[(S)-1-(amino-imino-methyl)-piperidin-3-ylmethylcarbamoyl]-2-benzyloxycarbonylamino-propionyl]-butyl-amino]propionic acid, ethyl [[(S)-3-[4-(amino-imino-methyl)-morpholin-2-ylmethylcarbamoyl]-2-benzyloxycarbonylamino-propionyl]-cyclopropyl-amino]acetate, ethyl [[(S)-3-[4-(amino-imino-methyl)-morpholin-2-ylmethylcarbamoyl]-2-benzyloxycarbonylamino-propionyl]-butyl-amino]acetate, ethyl 3-[[(S)-3-[4-(amino-imino-methyl)-morpholin-2-ylmethylcarbamoyl]-2-benzyloxycarbonylamino-propionyl]-cyclopropylamino]-propionate, ethyl 3-[[(S)-3-[4-(amino-imino-methyl)-morpholin-2-ylmethylcarbamoyl]-2-benzyloxycarbonylamino-propionyl]-butyl-amino]propionate,

[[(S)-3-[4-(amino-imino-methyl)-morpholin-2-ylmethylcarbamoyl]-2-benzyloxycarbonylamino-propionyl]-cyclopropyl-amino]acetic acid, 3-[[(S)-3-[4-(amino-imino-methyl)-morpholin-2-ylmethylcarbamoyl]-2-benzyloxycarbonylamino-propionyl]-cyclopropyl-amino]propionic acid, 3-[[(S)-3-[4-(amino-imino-methyl)-morpholin-2-ylmethylcarbamoyl]-2-benzyloxycarbonylamino-propionyl]-butyl-amino]propionic acid, ethyl [[(S)-3-[(S)-1-(amino-imino-methyl)-piperidin-3-ylm-ethylcarbamoyl]-2-cyclohexylmethoxycarbonylamino-propionyl]-cyclopropyl-amino]-acetate,

[[(S)-3-[(S)-1-(amino-imino-methyl)-piperidin-3-ylmethyl-carbamoyl]-2-cyclohexylmethoxycarbonylamino-propionyl]-cyclopropyl-amino]-acetic acid, ethyl [[(S)-3-[(S)-1-(amino-imino-methyl)-piperidin-3-ylm-ethylcarbarnoyl]-2-(3-benzyl-ureido)-propionyl]-cyclopropyl-amino]acetate, ethyl [[(S)-3-[(S)-1 -(amino-imino-methyl)-piperidin-3-yl-methylcarbomyl]-2-(3-furan-2-yimethyl-ureido)-propionyl]-cyclopropylamino]-acetate, ethyl [[(S)-3-[(S)-1-(amino-imino-methyl)-piperidin-3-ylm-ethylcarbamoyl]-2-(3-butyl-ureido)-propionyl]-cyclopropyl-aminoJacetate, ethyl 3-[[(S)-3-[(S)-1-(amino-imino-methyl)-piperidin-3-yl-methylcarbamoyl]-2-(3-furan-2-ylmethyl-ureido)-propionyl]-butylamino]-propionate,

[[(S)-3-[(S)-1-(amino-imino-methyl)-piperidin-3-ylmethyl-carbamoyl]-2-(3-benzyl-ureido)-propionyl]-cyclopropyl-amino]-acetic acid,

[[(S)-[(S)-1-(amino-imino-methyl)-piperidin-3-ylmethyl-carbamoyl]-2-(3-furan-2-ylmethyl-ureido)propionyl]-cyclopropylamino]-acetic acid,

[[(S)-3-[(S)-1-(amino-imino-methyl)-piperidin-3-ylmethyl-carbamoyl]-2-(3-n-butyl-ureido)-propionyl]-cyclopropyl-amino]-acetic acid,

[[(S)-[(S)-1-(amino-imino-methyl)-piperidin-3-ylmethyl-carbamoyl]-2-(3-furan-2-ylmethyl)-ureido)-propionyl]-n-butylamino]-propionic acid, ethyl [[(S)-3-[(S)-1-(amino-imino-methyl)-piperidin-3-ylm-ethylcarbamoyl]-2-pentanoylamino-propionyl]-cyclopropyl-amino]acetate, ethyl [[(S)-3-[(S)-1-(amino-imino-methyl)-piperidin-3-ylm-ethylcarbamoyl]-2-hexanoylamino-propionyl]-cyclopropyl-amino]-acetate, ethyl [[(S)-3-[(S)-1-(amino-imino-methyl)-piperidin-3-ylm-ethylcarbamoyl]-2-(4-chloro-pyridin-2-ylcarbonylamino)-propionyl]-cyclopropyl-amino]-acetate, ethyl [[(S)-3-[(S)-1-(amino-imino-methyl)-piperidin-3-ylm-ethylcarbamoyl]-2-benzoylamino-propionyl]-cyclopropyl-amino]acetate, ethyl [[(S)-3-[(S)-1-(amino-imino-methyl)-piperidin-3-ylm-ethylcarbarnoyl]-2-benzyloxycarbonylamino-propionyl]-cyclopropyl-amino]acetate,

[[(S)-3-[(S)-1-(amino-imino-methyl)-piperidin-3-ylmethyl-carbamoyl]-2-hexanoylamino-propionyl]-cyclopropyl-amino]-acetic acid,

[[(S)-3-[(S)-1-(amino-imino-methyl)-piperidin-3-ylmethyl-carbamoyl]-2-(4-chloro-pyridin-2-ylcarbonylamino)-propionyl]-cyclopropyl-amino]-acetic acid,

[[(S)-3-[(S)-1-(amino-imino-methyl)-piperidin-3-ylmethyl-carbamoyl]-2-benzoylamino-propionyl]-cyclopropyl-amino]-acetic acid,

[[(S)-3-[(S)-1-(amino-imino-methyl)-piperidin-3-ylmethyl-carbamoyl]-2-benzylcarbonylamino-propionyl]-cyclopropyl-amino]acetic acid, (S)-N4-[(S)-1-(amino-imino-methyl)-piperidin-3-ylm-ethyl]-2 -tert-butoxycarbonylamino-N1-cyclopropyl-N1-(2-pyrazin-2 -ylcarbonylamino)-succinamide, (S)-N4-[(S)-1-(amino-imino-methyl)-piperidin-3-ylmethyl] -N1-cyclopropyl-2-(3-indol-3-yl-propionylamino)-N1-(2-pyrazin-2 -ylcarbonylamino-ethyl)-succinamide, methyl (S)-4-[(S)-2-[(S)-1-(amino-imino-methyl)-piperi-din-3-ylmethylcarbonyl]-1-[cyclopropyl-(2-pyrazin-2-yl-carbonylaminoethyl)-carbamoyl]-ethylcarbamoyl]-4-hydroxy-butyrate, (S)-2-[(S)-2-acetylamino-3-indol-3-yl-propionylamino]-N4-[(S)-1-(amino-imino-methyl)-piperidin-3-ylmethyl]-N1-cyclopropyl-N1-(2-pyrazin-2-ylcarbonylamino-ethyl)-succinamide, (S)-N4-[(S)-1-(amino-imino-methyl)-piperidin-3-ylmethyl] -N1-cyclopropyl-2-phenoxyacetylamino-N1-(2-pyrazin-2-ylcarbonylaminoethyl)-succinamide, benzyl 2-[[(S)-3-[(S)-1-(amino-imino-methyl)-piperidin-3-ylmethylcarbamoyl]-2-morpholin-4-ylsulphonylamino-propionyl]-cyclopropyl-amino]-ethylcarbamate and (S)-N4-[(S)-1-(amino-imino-methyl)-piperidin-3-ylmethyl] -N1 -cyclopropyl-2-morpholin-4-ylsulphonylamino-N1-(2-pyrazin-2 -ylcarbonylamino-ethyl)-succinamide.

Further examples of compounds Ia are:

(S)-N4-[(S)-1-(Amino-imino-methyl)-piperidin-3-ylm-ethyl]-N1 -cyclopropyl-2-morpholin-4-ylsulphony-lamino-N1-[2-(6-oxo-1,4,5,6 -tetrahydro-pyridazin-3-yl-carbonylamino)-ethyl]-succinamide, (S)-N4-[(S)-1-(amino-imino-methyl)-piperidin-3-ylmethyl] -N1 -[2-(3-amino-pyrazin-2-ylcarbonylamino)-ethyl]-N1-cyclopropyl-2 -morpholin-4-ylsulphonylamino-succinamide, (S)-N4-[(S)-1-(amino-imino-methyl)-piperidin-3-ylmethyl] -N1 -cyclopropyl-N1-(2-methoxyacetylamino-ethyl)-2-morpholin-4 -ylsulphonylamino-succinamide, (S)-N4-[(S)-1-(amino-imino-methyl)-piperidin-3-ylmethyl] -N-1 -cyclopropyl-N1-(2-morpholin-4-ylacetylamino-ethyl)-2-morpholin-4 -ylsulphonylamino-succinamide, (S)-N4-[(S)-1-(amino-imino-methyl)-piperidin-3-ylmethyl] -N1 -cyclopropyl-N1-[2-(4-methyl-piperazin-1-ylacety-lamino)-ethyl]-2 -morpholin-4-ylsulphonylamino-succinamide, (S)-N4-[(S)-1-(amino-imino-methyl)-piperidin-3-ylm-ethyl-N1 -cyclopropyl-N1-[2-(3-methoxy-propiony-lamino)-ethyl]-2-morpholin-4 -ylsulphonylamino-succinamide, (S)-N4-[(S)-1-(amino-imino-methyl)-piperidin-3-ylmethyl] -N1 -cyclopropyl-N1-(2-imidazol-1-ylacetylamino-ethyl)-2-morpholin-4 -ylsulphonylamino-succinamide, (E)- and (Z)-4-[2-[[(S)-3-[(S)-1-(amino-imino-methyl)-pip-eridin-3-ylmethylcarbamoyl]-2-morpholin-4-ylsulphony-laminopropionyl]-cyclopropyl-amino]-ethylcarbamoyl]-4-hydroxyimino-butyric acid, (S)-N1-(2-amino-ethyl)-N4-[(S)-1-(amino-imino-meth-yl)piperidin-3-ylmethyl]-N1-cyclopropyl-2-morpholin-4 -yl-sulphonylamino-succinamide, (S)-N4-[(S)-1-(amino-imino-methyl)-piperidin-3-ylmethyl] -N1 -cyclopropyl-N1-[2-(4-methyl-piperazin-1-ylsulpho-nylamino)-ethyl]-2 -morpholin-4-ylsulphonylamino-suc-cinamide, (S)-N4-[(S)-1-(amino-imino-methyl)-piperidin-3-ylm-ethyl-N1 -cyclopropyl-2-morpholin-4-ylsulphonylamino-N1-(2-morpholin-4 -ylsulphonylamino-ethyl)-succina-mide, (S)-N4-[(S)-1-(amino-imino-methyl)-piperidin-3-ylmethyl] -N1 -cyclopropyl-2-(3-methoxy-propionylamino )-N1-(2-pyrazin-2 -ylcarbonylamino-ethyl)-succinamide, (S)-N4-[(S)-1-(amino-imino-methyl)-piperidin-3-ylmethyl] -N1-cyclopropyl-2-methoxyacetylamino-N1-(2-pyrazin-2 -ylcarbonylaminoethyl)-succinamide, (S)-N4-[(S)-1-(amino-imino-methyl)-piperidin-3-ylmethyl] -N1 -cyclopropyl-2-(4-methyl-piperazin-1-ylacety-lamino)-N1-(2-pyrazin-2-ylcarbonylaminoethyl)-succi-namide, (S)-N4-[(S)-1-(amino-imino-methyl)-piperidin-3-ylmethyl] -2-[(S)-2-amino-3-phenyl-propionylamino]-N1-cyclo-propyl-N1-(2-pyrazin-2-ylcarbonylamino-ethyl)-succina-mide, (S)-N4-[(S)-1-(amino-imino-methyl)-piperidin-3-ylmethyl-2-[(R)-2-amino-3-phenyl-propionylamino]-N1-cyclopropyl-N1-(2-pyrizin-2-ylcarbonylamino-ethyl)-succinamide, (S)-N4-[(S)-1-(amino-imino-methyl)-piperidin-3-ylmethyl] -N1 -cyclopropyl-2-[2-(4-hydroxy-piperidin-1-yl)-acetylamino]-N1-(2-pyrazin-2-ylcarbonylamino-ethyl)-succinamide, (S)-N4-[(S)-1-(amino-imino-methyl)-piperidin-3-ylmethyl] -N1 -cyclopropyl-2-(2-imidazol-1-yl-acetylamino)-N1-(2-pyrazin-2 -ylcarbonylamino-ethyl)-succinamide, (S)-N4-[(S)-1-(amino-imino-methyl)-piperidin-3-ylmethyl] -N1 -cyclopropyl-2-[2-(2-oxo-piperidin-1-yl)-acetylamino]-N1-(2-pyrazin-2-ylcarbonylamino-ethyl)-succinamide, (S)-N4-[(S)-1-(amino-imino-methyl)-piperidin-3-ylmethyl] -N1 -cyclopropyl-2-(3-dimethylamino-propionylamino)-N1-(2-pyrazin-2 -ylcarbonylamino-ethyl)-succinamide, (S)-N4-[(S)-1-(amino-imino-methyl)-piperidin-3-ylmethyl] -N1 -cyclopropyl-2-(2-dimethylamino-acetylamino)-N1-(2-pyrazin-2 -ylcarbonylamino-ethyl)-succinamide, (S)-N4-[(S)-1-(amino-imino-methyl)-piperidin-3-ylmethyl] -N1 -cyclopropyl-2-(2,6-dimethyl-morpholin-4-ylacetylamino )-N1-(2-pyrazin- 2-ylcarbonylamino-ethyl)-succinamide, ethyl 3-[[(S)-3-[(S)-1-(amino-imino-methyl)-piperidin-3-ylmethylcarbamoyl]-2-butylamino-propionyl]-cyclopropyl-amino]propionate, 3-[[(S)-3-[(S)-1-(amino-imino-methyl)-piperidin-3-ylmethylcarbamoyl]-2-butylamino-propionyl]-cyclopropyl-amino]propionic acid,

[[(S)-2-amino-3-[(S)-1-(amino-imino-methyl)-piperidin-3-ylmethylcarbamoyl]-propionyl]-cyclopropyl-amino]-acetic acid, (S)-3-amino-N-[(S)-1-(amino-imino-methyl)-piperidin-3-ylmethyl]-4-azepan-1-yl-4-oxo-butyramide, (S)-N-[(S)-1-(amino-imino-methyl)-piperidin-3-ylmethyl]-4-azepan-1-yl-3-benzyloxycarbonylamino-4-oxo-butyramide, ethyl [[(S)-3-[(S)-1-(amino-imino-methyl)-piperidin-3-ylmethylcarbamoyl]-2-(3-diphenylmethyl-ureido)-propionyl] -cyclopropylamino]-acetate, ethyl [[(S)-3-[(S)-1-(amino-imino-methyl)-piperidin-3-ylmethylcarbamoyl]-2-(3-cyclohexylmethyl-ureido)-propionyl]-cyclopropyl-amino]-acetate, (S)-N-[(S)-1-(amino-imino-methyl)-piperidin-3-ylmethyl]-4-azepan-1-yl-3-(3-benzyl-ureido)-4-oxo-butyramide, methyl (S)-2-[3-[(S)-1-[(S)-(amino-imino-methyl)-piperidin-3-ylmethylcarbamoylmethyl]-2-azepan-1-yl-2-oxo-ethyl]-ureido]-3-phenylpropionate, methyl (R)-2-[3-[(S)-1-[(S)-(amino-imino-methyl)-piperidin-3-ylmethylcarbamoylmethyl]-2-azepan-1-yl-2-oxo-ethyl]-ureido]-3-phenylpropionate,

[[(S)-3-[(S)-1-(amino-imino-methyl)-piperidin-3-ylmethylcarbamoyl]-2-(3-diphenylmethyl-ureido)-propionyl]-cyclopropylamino]-acetic acid,

[[(S)-3-[(S)-1-(amino-imino-methyl)-piperidin-3-ylmethylcarbamoyl]-2-(3-cyclohexylmethyl-ureido )-propionyl]-cyclopropylamino]-acetic acid, (S)-2-[3-[(S)-1-[(S)-(amino-imino-methyl)-piperidin-3-ylmethylcarbamoylmethyl]-2-azepan-1-yl-2-oxo-ethyl]-ureido]-3-phenylpropionic acid, (R)-2-[3-[(S)-1-[(S)-(amino-imino-methyl)-piperidin-3-ylmethylcarbamoylmethyl]-2-azepan-1-yl-2-oxo-ethyl]-ureido]-3-phenylpropionic acid,

[[(S)-2-benzyloxycarbonylamino-3-[(S)-1 -(ethoxycarbonylamino-imino-methyl)-piperidin-3-ylmethylcarbamoyl]-propionyl]-cyclopropyl-amino]-acetic acid,

[[(S)-2-benzyloxycarbonylamino-3-[4 -(ethoxycarbonylamino-imino-methyl)-morpholin-2-ylmethylcarbamoyl]-propionyl]-cyclopropyl-amino]-acetic acid, ethyl [[(S)-3-[(S)-1-amino-imino-methyl)-piperidin-3-ylmethylcarbamoyl]-2-(2-chloro-acetylamino )-propionyl]-cyclopropyl-amino]acetate and

[[(S)-3-[(S)-1-amino-imino-methyl)-piperidin-3-ylmethylcarbamoyl]-2-(2-chloro-acetylamino)-propionyl]-cyclopropyl-amino]acetic acid.

Examples of compounds Ib are:

N-[(S)-1-(Amino-imino-methyl)-piperidin-3-ylmethyl]-2 [(S)-4-cyclopentyl-1-naphthalen-2-ylsulphonyl-3,6-dioxo-piperazin-2-yl]-acetamide,

[3-[(S)-1-(amino-imino-methyl)-piperidin-3-ylmethylcarbamoylmethyl]-4-butylsulphonyl-2-oxo-piperazin-1-yl] acetic acid and N-[(S)-1-(amino-imino-methyl)-piperidin-3-ylmethyl]-2-[(S)-2,6-dioxo-4-butyl-piperazin-2-yl]-acetamide.

Further examples of compounds Ib are:

N-[(S)-1-(Amino-imino-methyl)-piperidin-3-ylmethyl]-2-[(S)-4-cyclopropyl-3,6-dioxo-1-(3-phenyl-propyl)-piperazin-2-yl]-acetamide, N-[(S)-1-(amino-imino-methyl)-piperidin-3-ylmethyl]-2-[(S)-1-naphthalen-2-ylsulphonyl-3,6-dioxo-piperazin-2-yl]-acetamide, N-[(S)-1-(amino-imino-methyl)-piperidino3-ylmethyl]-2-[(2S,5S)-5-hydroxymethyl-1-naphthalen-2-ylsulphonyl-3,6-dioxopiperazin-2-yl]-acetamide, (2S,5R)- and (2S,5S)-(5-benzyl-3,6-dioxo-4-propyl-piperazin-2 -yl)-acetic acid (S)-1-(amino-imino-methyl)-piperidin-3-ylmethylamide, ethyl (S)-[2-[(S)-1-(amino-imino-methyl)-piperidin-3-ylmethylcarbamoylmethyl]-4-cyclopropyl-3,6-dioxo-piperazin-1-yl]-acetate,

[(S)-2-[(S)-1-(amino-imino-methyl)-piperidin-3-ylmethylcarbamoylmethyl]-4-cyclopropyl-3,6-dioxo-piperazin-1-yl]-acetic acid and (R)- and (S)-(2,4-dimethyl-1-naphthalen-2-ylsulphonyl-3-oxo-piperazin-2-yl)-acetic acid (S)-1-(amino-imino-methyl)-piperidin-3-ylmethylamide.

The following are preferred compounds of formula I:

[[(S)-3-[4-(Amino-imino-methyl)-morpholin-2-ylmethylcarbamoyl]-2-benzyloxycarbonylamino-propionyl]-butyl-amino]-acetic acid,

[[(S)-3-[(S)-1-(amino-imino-methyl)-piperidin-3-ylmethylcarbamoyl]-2-pentanoylamino-propionyl]-cyclopropylamino]-acetic acid, (S)-N4-[(S)-1-(amino-imino-methyl)-piperidin-3-ylmethyl] -N1-cyclopropyl-N1-(2-pyrazin-2-ylcarbonylaminoethyl)-2-pyrimidin-2 -ylsulphanylacetylamino-succinamide, (S)-N4-[(S)-1-(amino-hydroxyimino-methyl)-piperidin-3-ylmethyl]-N1-cyclopropyl-2-(naphthalen-2-ylsulphonylamino)-N1-[2 -(pyrazin-2-ylcarbonylamino)-ethyl]-succinamide, (S)-N4-[(S)-1-(amino-imino-methyl)-piperidin-3-ylmethyl] -N1-cyclopropyl-2-morpholin-4-ylsulphonylamino-N1-[2-(6-oxo-1,6 -dihydro-pyridazin-3-ylcarbonylaminoethyl]-succinamide and N-[(S)-1-(amino-imino-methyl)-piperidin-3-ylmethyl]-2 [(S)-4-cyclopropyl-1-naphthalen-2-ylsulphonyl-3,6-dioxo-piperazin-2-yl]acetamide.

The following compounds are also preferred:

(S)-N4-[(S)-1-(Amino-imino-methyl)-piperidin-3-ylmethyl]-N1-cyclopropyl-2-morpholin-4-ylacetylamino-N1-(2-pyrazin-2 -ylcarbonylamino-ethyl)-succinamide, ethyl 3-[[(S)-3-[(S)-1-(amino-imino-methyl)-piperidin-3-ylmethylcarbamoyl]-2-(3-phenyl-propylamino)propionyl]-cyclopropylamino]-propionate, 3-[[(S)-3-[(S)-1-(amino-imino-methyl)-piperidin-3-ylmethylcarbamoyl]-2-(3-phenyl-propylamino )-propionyl]-cyclopropylamino]-propionic acid and 3-[[(S)-3-[(S)-1-(amino-imino-methyl)-piperidin-3-ylmethylcarbamoyl]-2-morpholin-4-ylsulphonylamino-propionyl]cyclopropyl-amino]-propionic acid.

The compounds in accordance with the invention are manufactured manner known per se by a) reacting an acid of the formula

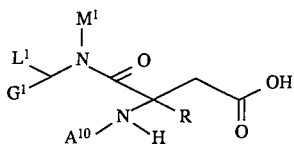   II with an amine of the formula $H_2NCH_2Q$   III or a salt thereof optionally with intermediary protection of functional groups present in the groups $G^1$, $M^1$ and $A^{10}$ (in II) and Q (in III), or b) reacting an amine of the formula

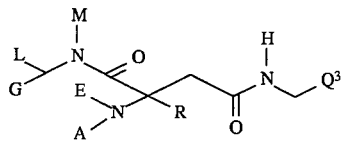   X wherein Q is a group of the formula

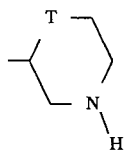   ($Q^{31}$)

or

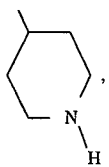   ($Q^{32}$), with an agent which introduces the optionally hydroxylated amidine group $—C(NR^7)NHR^6$, or c) reacting an amine of the formula

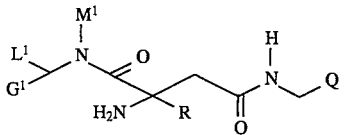   XX with an agent which introduces the group $A^{10}$, or d) cyclizing an amino acid of the formula

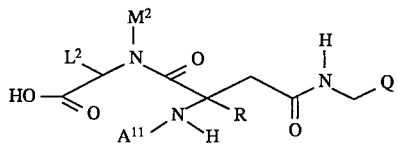   XXX or of the formula

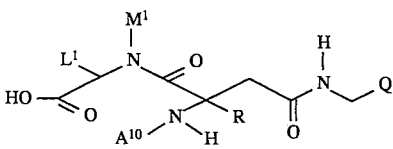   Ia1 to a compound of formula Ib, or e) for the manufacture of a carboxylic acid of formula Ib in which $M^2$ is carboxy-lower-alkyl, cleaving the corresponding lower-alkyl ester, and f) if desired, functionally modifying a reactive group present in a compound of formula I obtained, and g) if desired, converting a compound of formula I into a physiologically compatible salt or converting a salt of a compound of formula I into the free acid or base.

Conveniently, the acid II is reacted in a solvent such as dimethylformamide (DMF) or methylene chloride in the presence of a base such as 4-ethylmorpholine, triethylamine, ethyldiisopropylamine (Hünig base) or 1,8-diazabicyclo(5.4.0)undec-7-ene (DBU) with a salt of a compound of formula III, e.g. a trifluoroacetate, bisulphite, nitrate, hydrochloride or hydroiodide and with benzotriazol-1-yloxytris(dimethylamino)phosphonium hexafluorophosphate (BOP) at room temperature. Functional groups such as COOH, $NH_2$ and OH which are present in the compounds II and III and which are to be intermediately protected can be protected in the form of lower-alkylOCO groups, of benzylOCO or azide groups or of benzyloxy groups. The cleavage of a protected carboxy group such as $COOCH_3$ or $COOC_2H_5$ to COOH can be effected with sodium hydroxide in ethanol. The conversion of the benzylOCONH or $N_3$ group into the free amino group can be carried out by catalytic (Pd/C) hydrogenation in ethanol.

According to process variant b) for the manufacture of a compound of formula I in which $R^6$ and $R^7$ (in group Q) are hydrogen, the corresponding compound of formula X can be reacted in a solvent such as DMF or methanol in the presence of a base such as triethylamine with formamidinesulphonic acid or 3,5-dimethyl-1-pyrazolyl-formamidimium nitrate, conveniently at a temperature up to 50° C.

For the manufacture of a compound I in which $R^6$ or $R^7$ (in group Q) is OH, a compound X in a solvent such as methylene chloride can be reacted while cooling with cyanogen bromide and then with hydroxylamine hydrochloride in the presence of an amine such as triethylamine.

Variant c) can be carried out by reacting an amine XX in a solvent such as DMF in the presence of a base such as ethylmorpholine with a compound of the formula $ClC(O)OR^2$ or $ClC(O)R^2$, e.g. with cyclohexylmethyl chloroformate. When an amine XX in a solvent such as acetonitrile is reacted with sodium bicarbonate and an activated carbamate, e.g. 2,5-dioxopyrrolidin-1-yl benzylcarbamate, then a urethane of formula Ia in which $A^{10}$ is a group $—C(O)NHR^{22}$ is obtained. When an amine II in a solvent such as methylene chloride is reacted with a carboxylic acid, e.g. pyrimidine-2-thioacetic acid, in the presence of a base such as Hünig base and BOP, then a compound of formula Ia in which $A^{10}$ stands for a group $—C(O)R^2$, wherein $R^2$ is e.g. -(O or S)-(aryl, heteroaryl or cycloalkyl) bonded via lower-alkylene, is obtained.

The cyclization d) can be carried out in a solvent such as DMF in the presence of a base such as 4-ethylmorpholine and BOP.

The cleavage e) of a lower-alkyl carboxylic acid ester to the corresponding carboxylic acid of formula Ib in which $M^2$ is carboxy-lower-alkyl can be carried out in a solvent such as aqueous ethanol using an ion exchanger in Cl- form.

The following can be mentioned as functional modifications in variant f):

1. The saponification of an ester group such as ethoxycarbonyl, e.g. in THF by means of a base such as aqueous LiOH;
2. the cleavage of the Z group (benzyloxycarbonyl) in a Z-protected amino group present e.g. in group G;
3. the conversion of the free amino group obtained under 2. into a group NHC(O)-(aryl or heteroaryl) or into a group $NHSO_2N(Het)$, e.g. by reaction with a carboxylic acid of the formula G-COOH or, respectively, with $ClSO_2-N(Het)$.

The starting materials used above can be prepared in a manner known per se, e.g. according to the following Reaction Schemes:

Reaction Scheme 1

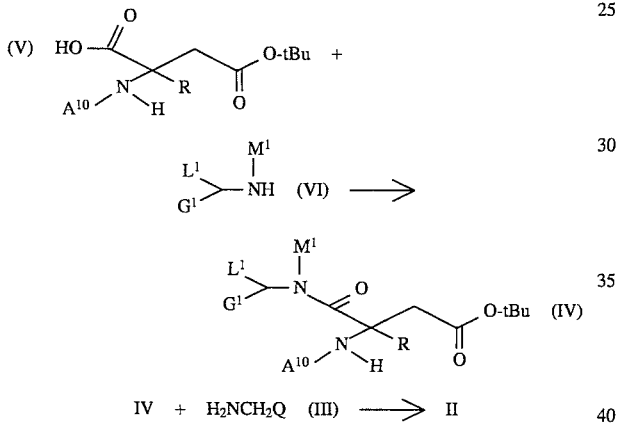

Reaction Scheme 2

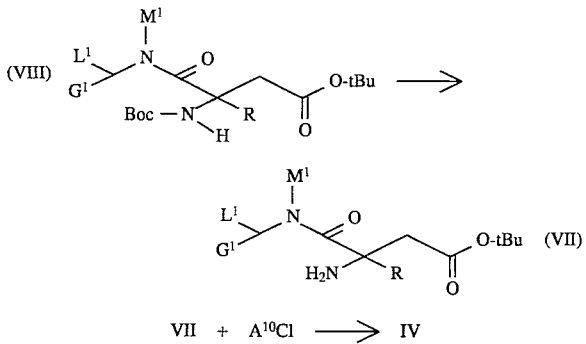

An amine XX can be obtained e.g. by cleaving off the Z group in a compound of Ia in which the group $A^{10}$ is a benzyloxycarbonyl group.

Compounds XXX are described in EP-A-468231. They can be prepared like the compounds of formula Ia.

Ester starting materials in process variant e) can be prepared as follows:

Reaction Scheme 3

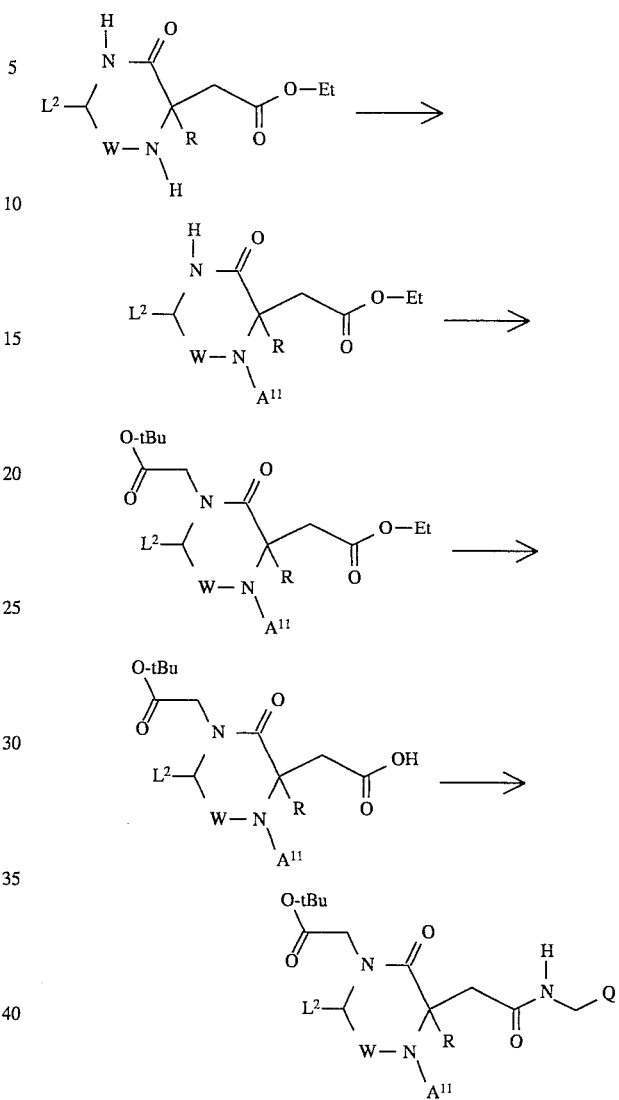

Moreover, many of the Examples hereinafter contain detailed information concerning the preparation of certain starting materials and intermediates.

The compounds of formula I, their solvates and their salts inhibit not only thrombin-induced platelet aggregation, but also thrombin-induced clotting of fibrinogen in blood plasma. The said compounds influence not only platelet-induced, but also plasmatic blood clotting. They therefore prevent especially the formation of hyaline thrombin and of platelet-rich thrombin and can be used in the control or prevention of illnesses such as thrombosis, stroke, cardiac infarct, inflammation and arterio-sclerosis. Further, these compounds have an effect on tumour cells and prevent the formation of metastases. Accordingly, they can also be used as antitumour agents.

A differential inhibition of thrombin and other serine proteases by the above compounds is desirable in order to obtain compounds having as high a specificity as possible and at the same time to avoid possible side-effects. Alongside other tested serine proteases the ratio of the inhibition of trypsin to the inhibition of thrombin was taken as the general measurement for the specificity of a compound (q in the Table hereinafter), because trypsin as the most unspecific serine protease can be readily inhibited by the widest variety of inhibitors. In order for the inhibition of thrombin and trypsin to be directly comparable in spite of the use of different substrates, the inhibition constant $K_i$ independent of substrate and enzyme concentration was determined as the measurement of the inhibition.

Specific chromogenic peptide substrates can be used to determine the inhibition of the catalytic activity of the above proteases. The inhibition of the amidolytic activity of thrombin and trypsin by the above guanidines was determined as described hereinafter.

The measurements were carried out on microtitre plates at room temperature. For this, in each well of the plate 150 μl of buffer (50 mM Tris, 100 mM NaCl, 0.1% polyethylene glycol; pH 7.8) were mixed with 50 μl of the inhibitor dissolved in DMSO and diluted in the buffer, and 25 μl of human thrombin (0.5 nM final conc.) were added. After incubation for 10 minutes the reaction was started by the addition of chromogenic substrate S-2238 (H-D-Phe-Pip-Arg-paranitroaniline from Kabivitrum; 10 or 50 μm final conc.) and the hydrolysis of the substrate was followed spectrophotometrically on a kinetic microtiter plate reader for 5 minutes. After graphical presentation of the inhibition curves the Ki values were determined according to the method described in Blochem. J. 55, 1955, 170–171. The inhibition of trypsin was effected analogously, but using the substrate S-2251 (H-D-Val-Leu-Lys-paranitroaniline) in 200 and 750 μM final concentration.

The results will be evident from the following Table:

| Product of Example | $K_i$ (μM) thrombin | $K_i$ (μM) trypsin | q |
| --- | --- | --- | --- |
| 1 | 1.2 | 70 | 58 |
| 2a | 0.017 | 29 | 1706 |
| 2b | 0.61 | 56 | 92 |
| 2c | 0.077 | 30 | 390 |
| 3 | 0.012 | 19 | 1583 |
| 4a | 0.079 | 83 | 1051 |
| 4b | 0.064 | 28 | 438 |
| 4c | 0.3 | 100 | 333 |
| 5a | 8.9 | 231 | 26 |
| 5b | 0.03 | 150 | 5000 |
| 5c | 0.054 | 29 | 537 |
| 5d | 0.13 | 12 | 92 |
| 6a | 0.45 | 140 | 311 |
| 6b | 0.0035 | 65 | 18571 |
| 6c | 0.33 | 92 | 279 |
| 6d | 0.94 | 85 | 90 |
| 7 | 2 | 50 | 25 |
| 8 | 0.017 | 27 | 1588 |
| 9a | 1.3 | 95 | 73 |
| 9b1 | 1.5 | 80 | 53 |
| 10 | 0.25 | 51 | 204 |
| 11 | 0.043 | 35 | 814 |
| 13a | 2.7 | 70 | 26 |
| 13b | 0.41 | 75 | 183 |
| 13d | 4.7 | 23.5 | 5 |
| 13e | 2.6 | 91 | 35 |
| 14a | 0.019 | 64 | 3368 |
| 14b | 0.036 | 25 | 694 |
| 14c | 0.057 | 50 | 877 |
| 14d | 0.25 | 83 | 332 |
| 14e | 0.081 | 69 | 852 |
| 15 | 0.0018 | 13 | 7222 |
| 16 | 0.11 | 14 | 127 |
| 17 | 1.3 | 96 | 74 |
| 18 | 2.2 | 590 | 268 |
| 19 | 0.0069 | 3.1 | 449 |
| 20 | 0.00086 | 4.5 | 5233 |
| 21a | 0.0023 | 8.9 | 3870 |
| 21b | 0.0072 | 14 | 1944 |
| 21c | 0.0061 | 15 | 2459 |
| 21d | 0.0013 | 25 | 19231 |
| 22 | 0.0015 | 16.5 | 11000 |
| 23 | 0.0046 | 13 | 2826 |
| 24 | 0.0012 | 7.1 | 5917 |
| 25 | 0.0013 | 7.2 | 5538 |

The compounds of formula I have a low toxicity. Thus, the products of the Examples enumerated in the Table have an LD50 of 125–500 mg/kg in mice upon intravenous administration.

As mentioned earlier, medicaments containing a compound of formula I, a solvate or salt thereof are likewise objects of the present invention, as is a process for the production of such medicaments which comprises bringing one or more of said compounds, solvates or salts and, if desired, other therapeutically valuable substances into a galenical dosage form. The medicaments can be administered enterally as dragées, hard and soft gelatine capsules, solutions, emulsions or suspensions, or rectally, e.g. in the form of suppositories, or as a spray. The administration can, however, also be effected parenterally, e.g. in the form of injection solutions.

For the production of tablets, coated tablets, dragées and hard gelatine capsules, the active substance can be mixed with pharmaceutically inert, inorganic or organic excipients. Lactose, maize starch or derivatives thereof, talc, stearic acid or its salts can be used e.g. as such excipients for tablets, coated tablets, dragées and hard gelatine capsules. Suitable excipients for soft gelatine capsules are e.g. vegetable oils, waxes, fats, semi-solid and liquid polyols; depending on the nature of the active sub-stance no excipients are, however, usually required in the case of soft gelatine capsules. Suitable excipients for the production of solutions and syrups are e.g. water, polyols, saccharose, invert sugar and glucose, suitable excipients for injection solutions are e.g. water, alcohols, polyols, glycerol and vegetable oils and suitable excipients for suppositories are natural or hardened oils, waxes, fats, semi-liquid or liquid polyols. The pharmaceutical preparations can also contain preservatives, solubilizers, stabili-zers, wetting agents, emulsifiers, sweeteners, colorants, flavor-ants, salts for varying the osmotic pressure, buffers, coating agents or antioxidants.

For the control or prevention of the illnesses mentioned above, the dosage of the active substance can vary within wide limits and will, of course, be fitted to the individual requirements in each particular case. In general, in the case of oral or parenteral, e.g. intravenous or subcutaneous, administration a dosage of about 0.1 to 20 mg/kg, preferably of about 0.5 to 4 mg/kg, per day should be appropriate for adults, although the upper limit just given can also be exceeded or reduced when this is shown to be indicated.

EXAMPLE 1

1.a) 3.6 g of tert.butyl (S)-3-benzyloxycarbonylamino-N-cyclopropyl-N-ethoxycarbonylmethyl-succinamate are dissolved in 36 ml of methylene chloride, treated at 0° with 40 ml of 4M hydrochloric acid in ethyl acetate and stirred for 5 hours. The solution is evaporated and the colourless residue is dissolved in 36 ml of DMF, treated with 5.1 ml of 4-ethylmorpholine, 3.55 g of benzotriazol-1-yloxytris(dimethylamino)phosphonium hexafluorophosphate (BOP) and 2.02 g of (S)-1-amidino-3-(aminomethyl)piperidine dihydrochloride (EP-A-468231: Example 60Ac) and stirred at room temperature overnight. The reaction mixture is evaporated and the residue is chromatographed on RP-18 with a water-acetonitrile gradient. The product fractions are evaporated and filtered with water-ethanol over an ion exchanger (Cl-form). 2.9 g of ethyl [[(S)-3-[(S)-1-(amino-imino-methyl)-piperidin-3-ylmethylcarbamoyl]-2-benzyloxycarbonylamino-propionyl]-cyclopropyl-amino]-acetate hydrochloride, MS (ion spray): 531.4 (M+H)$^+$, are isolated after evaporation.

1.B) Preparation of the starting material:

5.0 g of N-(dimethylaminopropyl)-N'-ethylcarbodiimide hydrochloride, 0.3 g of 4-dimethylaminopyridine and 3.7 g of N-cyclopropylglycine ethyl ester are added in succession to a solution of 8.0 g of N-Z-L-aspartic acid β-tert-butyl ester in 80 ml of methylene chloride and the mixture is stirred at room temperature for 17 hours. Then, the reaction mixture is poured into ice-cold 5% potassium hydrogen sulphate-10% potassium sulphate solution and extracted with ethyl acetate. The organic phases are washed with water, dried, evaporated and the residue is chromatographed on silica gel with hexane-ethyl acetate (3:1). 8.4 g of colourless, oily tert-butyl (S)-3-benzyloxycarbonylamino-N-cyclopropyl-N-ethoxycarbonylmethylsuccinamate, MS(FAB): 449.2 (M$^+$), are obtained.

EXAMPLE 2

2.A) The following compounds are prepared analogously to Example 1:

a) Ethyl 3-[[(S)-3-[(S)-1-(amino-imino-methyl)-piperidin-3-ylmethylcarbamoyl]-2-benzyloxycarbonylamino-propionyl]-cyclopropylamino]-propionate hydrochloride, MS (ion spray): 545.4 (M+H)$^+$, b) ethyl [[(S)-3-[(S)-1-(amino-imino-methyl)-piperidin-3-ylmethylcarbamoyl]-2-benzyloxycarbonylamino-propionyl]-butyl-amino]acetate hydrochloride, MS (ion spray): 547.5 (M+H)$^+$, c) ethyl 3-[[(S)-3-[(S)-1-(amino-imino-methyl)-piperidin-3-ylmethylcarbamoyl]-2-benzyloxycarbonylamino-propionyl]-butylamino]-propionate hydrochloride, MS (ion spray): 561.4 (M+H)$^+$.

2.B) Preparation of the starting materials:

The following intermediates are prepared analogously to Example 1B), but using N-cyclopropyl-β-alanine ethyl ester, N-butylglycine ethyl ester and, respectively, N-butyl-β-alanine ethyl ester in place of N-cyclopropylglycine ethyl ester:

a) tert-Butyl (S)-3-benzylcarbonylamino-N-cyclopropyl-N-(2-ethoxycarbonyl-ethyl)-succinamate, MS (FAB): 463.3 (M+H)$^+$, b) tert-butyl (S)-3-benzylcarbonylamino-N-butyl-N-ethoxy-carbonlmethyl-succinamate MS (ion spray): 465.4 (M+H)$^+$, c) tert-butyl (S)-3-benzylcarbonylamino-N-butyl-N-(2-ethoxycarbonyl-ethyl)-succinamate, MS (FAB): 479.3 (M+H)$^+$.

EXAMPLE 3

1.5 g of ethyl [[(S)-3-[(S)-1-(amino-imino-methyl)-piperidin-3-ylmethylcarbamoyl]-2-benzyloxycarbonylamino-propionyl]-cyclopropyl-amino]-acetate hydrochloride (Example 1) are dissolved in 15 ml of THF, treated with 7.9 ml of 1N lithium hydroxide solution and stirred at room temperature for 90 minutes. Then, the solution is treated with 7.9 ml of 1N hydrochloric acid and evaporated. The residue is chromatographed on RP-18 with a water-acetonitrile gradient. 0.63 g of colourless [[(S)-3-[(S)-1-(amino-imino-methyl)-piperidin-3-ylmethylcarbamoyl]-2-benzyloxycarbonylamino-propionyl]-cyclopropylamino]-acetic acid, MS (ion spray): 503.5 (M+H)$^+$, is obtained.

EXAMPLE 4

The following acids are obtained analogously to Example 3, but starting from the ester products of Example 2:

a) 3-[[(S)-3-[(S)-1-(Amino-imino-methyl)-piperidin-3-ylmethylcarbamoyl]-2-benzyloxycarbonylamino-propionyl]-cyclopropylamino]-propionic acid, MS (ion spray): 517.4 (M+H)$^+$, b) [[(S)-3-[(S)-1-(amino-imino-methyl)-piperidin-3-ylmethylcarbamoyl]-2-benzyloxycarbonylamino-propionyl]-butyl-amino]-acetic acid, MS (ion spray): 519.4 (M+H)$^+$, c) 3-[[(S)-3-[(S)-1-(amino-imino-methyl)-piperidin-3-ylmethylcarbamoyl]-2-benzyloxycarbonylamino-propionyl]-butyl-amino]propionic acid, MS (ion spray): 533.5 (M+H)$^+$.

EXAMPLE 5

The following compounds are prepared analogously to Example 1, but using rac-2-aminomethyl-4-morpholinecarboxamidine dihydrochloride in place of (S)-1-amidino-3-(aminomethyl)piperidine dihydrochloride:

a) from tert-butyl (S)-3-benzyloxycarbonylamino-N-cyclopropyl-N-ethoxycarbonylmethyl-succinamate, ethyl [[(S)-3-[4-(amino-imino-methyl)-morpholin-2-ylmethylcarbamoyl]-2-benzyloxycarbonylaminopropionyl]-cyclopropyl-amino]-acetate hydrochloride (1:1), MS (ion spray): 533.4 (M+H)$^+$, b) from tert-butyl (S)-3-benzyloxycarbonylamino-N-butyl-N-ethoxycarbonylmethyl-succinamate, ethyl [[(S)-3-[4-(amino-imino-methyl)-morpholin-2-ylmethylcarbamoyl]-2-benzyloxycarbonylaminopropionyl]-butyl-amino]-acetate hydrochloride (1:1), MS (ion spray): 549.4 (M+H)$^+$, c) from tert-butyl (S)-3-benzyloxycarbonylamino-N-cyclopropyl-N-(2-ethoxycarbonyl-ethyl)-succinamate, ethyl 3-[[(S)-3-[4-(amino-imino-methyl)-morpholin-2-ylmethylcarbamoyl]-2-benzyloxycarbonylaminopropionyl]-cyclopropyl-amino]-propionate hydrochloride (1:1), MS (ion spray): 547.5 (M+H)$^+$, d) from tert-butyl (S)-3-benzyloxycarbonylamino-N-butyl-N-(2-ethoxycarbonyl-ethyl)-succinamate, ethyl 3-[[(S)-3-[4-(amino-imino-methyl)-morpholin-2-ylmethylcarbamoyl]-2-benzyloxycarbonylaminopropionyl]-butyl-amino]-propionate hydrochloride (1:1), MS (ion spray): 563.5 (M+H)$^+$.

EXAMPLE 6

The following acids are obtained analogously to Example 3, but starting from the esters of Example 5:

a) [[(S)-3-[(S)-1-(Amino-imino-methyl)-piperidin-3-ylmethylcarbamoyl]-2-benzyloxycarbonylamino-propionyl]-cyclopropylamino]-propionic acid (1:1), MS (ion spray): 505.0 (M+H)$^+$, b) [[(S)-3-[4-(amino-imino-methyl)-morpholin-2-ylmethylcarbamoyl]-2-benzyloxycarbonylamino-propionyl]-butyl-amino]-acetic acid (1:1), MS (ion spray): 521.1 (M+H)$^+$, c) 3-[[(S)-3-[4-(amino-imino-methyl)-morpholin-2-ylmethylcarbamoyl]-2-benzyloxycarbonylamino-propionyl]-cyclopropyl-amino]propionic acid (1:1), MS (ion spray): 519.4 (M+H)⁺, d) 3-[[(S)-3-[4-(amino-imino-methyl)-morpholin-2-ylmethylcarbamoyl]-2-benzyloxycarbonylamino-propionyl]-butyl-amino]propionic acid (1:1), MS (ion spray): 535.4 (M+H)⁺.

EXAMPLE 7

7.A) 4.4. g of the product of Example 1.A) are dissolved in 44 ml of ethanol, treated with 7.7 ml of 1N hydrochloric acid und 0.44 g of Pd/C and hydrogenated at room temperature for 1 hour. After filtration and evaporation of the solution 3.4 g of colourless ethyl [[(S)-2-amino-3-[(S)-1-(amino-imino-methyl)-piperidin-3-ylmethylcarbamoyl]-propionyl]-cyclopropyl-amino]-acetate dihydrochloride, MS (ion spray): 397.4 (M+H)⁺, are obtained.

7.B) The following amines are obtained analogously to Example 7.A), but starting from the products of Example 2.A):

7.B)a) Ethyl 3-[[(S)-2-amino-3-[(S)-1-(amino-imino-methyl)piperidin-3-ylmethylcarbamoyl]-propionyl]-cyclopropyl-amino]propionate dihydrochloride, 7.B)b) ethyl 3-[[(S)-2-amino-3-[(S)-1-(amino-imino-methyl)piperidine-3-ylmethylcarbamoyl]-propionyl]-butyl-amino]-acetate dihydrochloride, 7.B)c) ethyl 3-[[(S)-2-amino-3-[(S)-1-(amino-imino-methyl)piperidin-3-ylmethylcarbamoyl]-propionyl]-butyl-amino]-propionate dihydrochloride, MS (ion spray): 427.4 (M+H)⁺.

7.C) The following amines are obtained analogously to Example 7.A), but starting from the product of Example 3 and, respectively, 4c):

7.C)a) [[(S)-2-Amino-3-[(S)-1-(amino-imino-methyl)-piperidin-3-ylmethylcarbamoyl]-propionyl]-cyclopropyl-amino]-acetic acid hydrochloride, MS (ion spray): 369.4 (M+H)⁺, 7.C)b) 3-[[(S)-2-amino-3-[(S)-1-(amino-imino-methyl)-piperidin-3-ylmethylcarbamoyl]-propionyl]-butyl-amino]-propionic acid hydrochloride, MS (ion spray): 399.4 (M+H)⁺.

7.D) 2.4 ml of 4-ethylmorpholine and 0.73 g of cyclohexylmethyl chloroformate are added to a solution of 1.7 g of the amine product of Example 7.A) in 18 ml of DMF and stirred at room temperature overnight. The reaction mixture is evaporated, treated with 1N hydrochloric acid and again evaporated, and the residue is chromatographed on RP-18 with an acetonitrile-water gradient. 1.6 g of ethyl [[(S)-3-[(S)-1-(amino-imino-methyl)-piperidin-3-ylmethylcarbamoyl]-2-cyciohexylmethoxycarbonylamino-propionyl]-cyclopropyl-amino]-acetate hydrochloride, MS (ion spray): 537.6 (M+H)⁺, are obtained after evaporation of the product fractions.

EXAMPLE 8

The following acid is obtained analogously to Example 3, but starting from the ester of Example 7.D):

[[(S)-3-[(S)-1-(Amino-imino-methyl)-piperidin-3-ylmethylcarbamoyl]-2-cyclohexylmethoxycarbonylaminopropionyl]cyclopropyl-amino]-acetic acid, MS (ion spray): 509.5 (M+H)⁺.

EXAMPLE 9

9.A) Preparation of the products:

9.A)a) 1.7 g of the amine product of Example 7.A) are dissolved in 17 ml of acetonitrile and 17 ml of water. 0.6 g of sodium bicarbonate and 1.35 g of 2,5-dioxo-pyrrolidin-1-yl benzylcarbamate are added thereto in succession and the mixture is stirred at room temperature for 17 hours. The reaction mixture is evaporated and the residue is purified on a RP-18 column with an acetonitrile-water gradient. 0.6 g of colourless ethyl [[(S)-3-[(S)-1-(amino-imino-methyl)-piperidin-3-ylmethylcarbamoyl]-2-(3-benzyi-ureido)-propionyl]-cyclopropylamino]-acetate hydrochloride, MS (ion spray): 530.5 (M+H)⁺, is isolated.

9.A)b) The following compounds are prepared in an analogous manner, but using the corresponding activated carbamates:

9.A)b)1) Ethyl [[(S)-3-[(S)-1-(amino-imino-methyl)-piperidin-3-ylmethylcarbamoyl]-2-(3-furan-2-ylmethyl-ureido)-propionyl]-cyclopropyl-amino]-acetate hydrochloride MS (ion spray): 520.5 (M+H)⁺, 9.A)b)2) ethyl [[(S)-3-[(S)-1-(amino-imino-methyl)-piperidin-3-ylmethylcarbamoyl]-2-(3-butyl-ureido)-propionyl]-cyclopropylamino]-acetate hydrochloride, MS (ion spray): 496.6 (M+H)⁺.

9.B) Preparation of the starting material:

9.B)a) 18.4 g of N,N'-disuccinimidyl carbonate are added in small portions at 5° C. within 5 minutes to a solution of 6.4 g of benzylamine in 150 ml of acetonitrile. The reaction mixture is stirred at room temperature and then evaporated. The residue is taken up in ethyl acetate and washed with water. The organic phase is dried, concentrated and the residue is recrystallized from methylene chlorideohexane. 11.3 g of colourless 2,5-dioxo-pyrrolidin-1-yl benzylcarbamate, MS (FAB): 133 (M- HO-Succ), are isolated.

9.B)b) The following activated carbamates are prepared in an analogous manner, but using the corresponding amines in place of benzylamine:

9.B)b)1) 2,5-Dioxo-tetrahydropyrrol-1-yl furan-2-ylmethylcarbamate, MS (FAB): 123 (M- HO-Succ), 9.B)b)2) 2,5-dioxo-pyrrolidin-1-yl pyridin-3-ylmethylcarbamate, MS (FAB): 151 (M- Succ), 9.B)b)3) 2,5-dioxo-pyrrolidin-1-yl butylcarbamate, MS (FAB): 214 (M).

EXAMPLE 10

The following ester is prepared analogously to Example 9, but starting from the amine from paragraph 7.B)c) and using the activated ester of paragraph 9.B)1:

Ethyl 3-[[(S)-3-[(S)-1-(amino-imino-methyl)-piperidin-3-ylmethylcarbamoyl]-2-(3-furan-2-ylmethyl-ureido)-propionyl]-butylamino]-propionate hydrochloride (1:1), MS (ion spray): 550.4 (M+H)⁺.

EXAMPLE 11

2.5 g of the product of Example 7.C)a) are dissolved in 25 ml of acetonitrile and 25 ml of water. 1.0 g of sodium bicarbonate and 2.3 g of 2,5-dioxo-pyrrolidin-1-yl benzylcarbamate are added thereto in succession and the mixture is stirred at room temperature for 5 hours.

The reaction mixture is evaporated and the residue is purified on a RP-18 column with an acetonitrile-water gradient. 0.8 g of colourless [[(S)-3-[(S)-1-(amino-iminomethyl)-piperidin-3-ylme thylcarbamoyl]2-(3-benzyl-ureido)-propionyl]-cyclopropyl-amino]-acetic acid, MS (ion spray): 502.4 (M+H)⁺, is isolated.

EXAMPLE 12

The following acids are prepared analogously to Example 3, but starting from the esters from Example 9.A)b)1), 9.A)b)2) and 10:

a) [[(S)-[(S)-1-(Amino-imino-methyl)-piperidin-3-ylmethylcarbamoyl]-2-(3-furan-2-ylmethyloureido)propionyl]-cyclopropylamino]-acetic acid, MS (ion spray): 492.5 (M+H)$^+$, b) [[(S)-3-[(S)-1-(amino-imino-methyl)-piperidin-3-ylmethylcarbamoyl]-2-(3-n-butyl-ureido)-propionyl]-cyclopropyl-amino]-acetic acid, MS (ion spray): 468.4 (M+H)$^+$, c) [[(S)-[(S)-1-(amino-imino-methyl)-piperidin-3-ylmethylcarbamoyl]-2-(3-furan-2-ylmethyl)-ureido )-propionyl]-n-butylamino]-propionic acid, MS (ion spray): 522.4 (M+H)$^+$.

EXAMPLE 13

A) The following compounds are prepared analogously to Example 1:

a) Ethyl [[(S)-3-[(S)-1-(amino-imino-methyl)-piperidin-3-ylmethylcarbamoyl]-2-pentanoylamino-propionyl]-cyclopropyl-amino]acetate hydrochloride, MS (ion spray): 481.5 (M+H)$^+$, b) ethyl [[(S)-3-[(S)-1-(amino-imino-methyl)-piperidin-3-ylmethylcarbamoyl]-2-hexanoylamino-propionyl]-cyclopropyl-amino]acetate hydrochloride, MS (ion spray): 495.6 (M+H)$^+$, c) ethyl [[(S)-3-[(S)-1-(amino-imino-methyl)-piperidin-3-ylmethylcarbamoyl]-2-(4-chloro-pyridin-2-ylcarbonylamino)propionyl] -cyclopropyl-amino]-acetate hydrochloride, MS (ion spray): 536.5 (M+H)$^+$, d) ethyl [[(S)-3-[(S)-1-(amino-imino-methyl)-piperidin-3-ylmethylcarbamoyl]-2-benzoylamino-propionyl]-cyclopropyl-amino]-acetate hydrochloride, MS (ion spray): 501.6 (M+H)$^+$, e) ethyl [[(S)-3-[(S)-1-(amino-imino-methyl)-piperidin-3-ylmethylcarbamoyl]-2-benzyloxycarbonylamino-propionyl]cyclopropyl-amino]-acetate hydrochloride, MS (ion spray): 515.5 (M+H)$^+$.

B) Preparation of the starting materials:

a) A solution of 16.6 g of t-butyl (S)-2-(2-tert-butoxyformamido)N-cyclopropyl-N-[(ethoxycarbonyl)methyl]succinamate (prepared analogously to the product of Example 1B) in 170 ml of dioxan is treated with 19.0 g of p-toluenesulphonic acid monohydrate and stirred at room temperature for 30 hours. Then, the solution is treated while cooling with 17.8 ml of pyridine and subsequently with 9.6 ml of valeroyl chloride and stirred at room temperature overnight. For the working-up, the reaction mixture is poured into ice-cold 5% potassium hydrogen sulphate-10% potassium sulphate solution and extracted with ethyl acetate. The organic phases are washed with dilute sodium chloride solution, dried and evaporated. 4.8 g of colourless tert-butyl (S)-N-cyclopropyl-N-ethoxycarbonylmethyl-3-pentanoylaminosuccinamate, MS (ion spray): 399.4 (M+H)$^+$, are isolated after chromatography of the residue on silica gel with hexane-ethyl acetate (2:1).

b) The following t-butyl esters are prepared analogously using the corresponding acid chlorides in place of valeroyl chloride:

b)1) tert-Butyl (S)-N-cyclopropyl-N-ethoxycarbonylmethyl-3 -hexanoylamino-succinamate, MS (FAB): 413 (M+H)$^+$, b)2) ethyl [[(S)-3-tert-butoxycarbonyl-2-(4-chloro-pyridin-2-ylcarbonylamino)-propionyl]-cyclopropyl-amino]-acetate, MS (FAB): 213 (M+H)$^+$, b)3) tert-butyl (S)-3-benzoylamino-N-cyclopropyl-N-ethoxycarbonylmethyl-succinamate, MS (FAB): 419 (M+H)$^+$, b)4) tert-butyl (S)-2-benzylcarbonylamino-N-cyclopropyl-N-ethoxycarbonylmethyl-succinamate, MS (ion spray): 433.1 (M+H)$^+$.

Example 14

The following acids are obtained analogously to Example 3, but starting from the esters of Example 13A):

a) [[(S)-3-[(S)-1-(Amino-imino-methyl)-piperidin-3-ylmethylcarbamoyl]-2-pentanoylamino-propionyl]-cyclopropyl-amino]acetic acid, MS (ion spray): 453.4 (M+H)$^+$, b) [[(S)-3-[(S)-1-(amino-imino-methyl)-piperidin-3-ylmethylcarbamoyl]-2-hexanoylamino-propionyl]-cyclopropyl-amino]-acetic acid, MS (ion spray): 467.4 (M+H)$^+$, c) [[(S)-3-[(S)-1-(amino-imino-methyl)-piperidin-3-ylmethylcarbamoyl]-2-(4-chloro-pyridin-2-ylcarbonylamino )-propionyl]cyclopropyl-amino]-acetic acid, MS (ion spray): 508.5 (M+H)$^+$, d) [[(S)-3-[(S)-1-(amino-imino-methyl)-piperidin-3-ylmethylcarbamoyl]-2-benzoylamino-propionyl]-cyclopropyl-amino]-acetic acid, MS (ion spray): 473.6 (M+H)$^+$, e) [[(S)-3-[(S)-1-(amino-imino-methyl)-piperidin-3-ylmethylcarbamoyl]-2-benzylcarbonylamino-propionyl]-cyclopropyl-amino]acetic acid, MS (ion spray): 487.4 (M+H)$^+$.

EXAMPLE 15

A solution of N-[N4-[[(S)-1-amidino-3-piperidinyl]methyl]-N2 -(naphthalen-2-ylsulphonyl)-L-asparaginyl]-N-cyclopropylglycine —(preparable from N-Boc-L-aspartic acid-β-t-butyl ester and N-cyclopropylglycine ethyl ester via t-butyl (S)-3(1-t-butoxyformamido-N-cyclopropyl-N-[(ethyloxycarbonyl)methyl]succinamate and via t-butyl (S)-N-cyclopropyl-N-[(ethoxycarbonyl)methyl]-3-(naphthalen-2-ylsulphonamido)succinamate)— in 30 ml of DMF is treated with 1.7 ml of 4-ethylmorpholine and 1.2 g of BOP and stirred at room temperature overnight. Then, the reaction mixture is evaporated, treated with 1N hydrochloric acid and again evaporated. The residue is chromatographed RP-18 with an aceton:itrile-water gradient. The product-containing fractions are concentrated and 0.7 g of N-[(S)-1-(amino-imino-methyl)-piperidin-3-ylmethyl]-2-[(S)-4-cyclopropyl-1-naphthalen-2-ylsulphonyl-3,6-dioxo-piperazin-2-yl]-acetamide hydrochloride, MS (ion spray): 541.5 (M+H)$^+$, is obtained.

EXAMPLE 16

In an analogous manner to Example 15, from:

(S)-N4-[(S)-1-(amino-imino-methyl)-piperidin-3-ylmethyl]-N1 -carboxymethyl-N1-cyclopentyl-2-(naphthalen-2-ylsulphonylamino)succinamide —(preparable from N-Boc-L-aspartic acid β-t-butyl ester and N-cyclopentylglycine ethyl ester via t-butyl (S)-3(1-t-butoxyformamido)-N-cyclopentyl-N-[(ethyloxycarbonyl)

methyl]succinamate and via t-butyl (S)-N-cyclopentyl-N-[(ethoxycarbonyl)methyl]-3-(naphthalen-2-ylsulphonamido)succinamate)— there is obtained N-[(S)-1-(amino-imino-methyl)-piperidin-3-ylmethyl]-2[(S)-4-cyclopentyl-1-naphthalen-2-ylsulphonyl-3,6-dioxopiperazin-2-yl]-acetamide hydrochloride, MS (ion spray): 569.4 (M+H)⁺.

Example 17

A) Preparation of the product:

0.8 g of (RS)-(4-tert-butoxycarbonylmethyl-1-butylsulphonyl-3-oxo-piperazin-2-yl)-acetic acid is dissolved in 15 ml of DMF, treated in succession with 1.3 ml of 4-ethylmorpholine, 0.92 g of BOP and 0.72 g of (S)-1-amidino-3-(aminomethyl)-piperidine dihydrochloride. The reaction mixture is stirred at room temperature overnight, then evaporated and the residue is chromatographed on RP-18 with a water-acetonitrile gradient. The product fractions are evaporated and filtered over an ion exchanger (Cl- form) with water-ethanol. Colourless [3-[(S)-1-(amino-imino-methyl)-piperidin-3-ylmethylcarbamoylmethyl]-4-butylsulphonyl-2-oxo-piperazin-1yl]acetic acid (1:1), MS (ion spray): 475.6 (M+H)⁺, is isolated after evaporation.

B) Preparation of the starting material:

a) 15.0 g of ethyl 2-piperazin-3-one acetate are dissolved in 150 ml of pyridine and treated at room temperature with 12.5 ml of 1-butanesulphochloride. The reaction mixture is stirred at room temperature overnight and then evaporated. After chromatography of the residue on silica gel with ethyl acetate-hexane there are obtained 23.1 g of colourless ethyl (RS)-(1-butylsulphonyl-3-oxo-piperazin-2-yl)-acetate, MS (FAB): 261 (M-OEt).

b) 520 mg of sodium hydride dispersion (60%) and a solution of 1.9 ml of tert-butyl bromoacetate in 30 ml of DMF are added in succession at −15° C. to a solution of 2.0 g of the material obtained under a) in 20 ml of EMF. The reaction mixture is stirred at room temperature, then treated with water and extracted with ethyl acetate. The organic phases are washed with water, dried and evaporated. The residue is chromatographed on silica gel with ethyl acetate-hexane and 1.8 g of colourless tert-butyl (RS)-3-ethoxycarbonyl-2-oxo-4-butylsulphonylpiperazin-1-ylacetate, MS (FAB): 375 (M-OEt), are isolated.

c) 1.7 g of the material obtained under b) are dissolved in 17 ml of THF, treated with 12 ml of 1N lithium hydroxide solution and stirred at room temperature for 2 hours. Then, 10 ml of acetic acid are added and the reaction mixture is evaporated. The residue is taken up in ethyl acetate., washed with ice-cold 5% potassium hydrogen sulphate-10% potassium sulphate solution and washed with water. The organic phases are dried and evaporated. 0.8 g of (RS)-(4-tert-butoxycarbonylmethyl-1-butylsulphonyl-3-oxo-piperazin-2-yl)-acetic acid, MS (ion spray): 391.3 (M–H)—, is obtained.

EXAMPLE 18

A solution of 1.3 g of ethyl [[(S)-3-[(S)-1-(amino-iminomethyl)piperidin-3-ylmethylcarbamoyl]-2-benzyloxycarbonylaminopropionyl]butyl-amino]-acetate hydrochloride (Example 2.A)b) are dissolved in 13 ml of ethanol and 13 ml of 1 N hydrochloric acid, treated with 0.13 g of Pd/C and hydrogenated at room temperature for 90 minutes. After filtration of the reaction mixture, evaporation of the filtrate and chromatography of the residue on RP-18 with an acetonitrile-water gradient 0.4 g of N-[(S)-1-(amino-iminomethyl)-piperidin-3-ylmethyl]-2-[(S)-2,6-dioxo-4-butyl-piperazin-2-yl]-acetamide hydrochloride, MS (ion spray): 367.4 (M+H⁺, is obtained.

EXAMPLE 19

4.1 g of cyclopropyl-2-(pyrazin-2-ylcarbonylamino)ethylamine hydrochloride (1:2), 4.98 g of Z-Asp(OtBu)-OH and 7.37 g of BOP are dissolved in 100 ml of methylene chloride and treated with 10.06 ml of Hünig's base while stirring. After stirring at room temperature for 2 hours tlne mixture is taken up in ether and washed with water. After evaporation of the ethyl acetate phase and chromatography of the residue on silica gel 7.06 g of tert-butyl (S)-2-benzyloxycarbonylamino-N 1-cyclopropyl-N1-(2-pyrazin-2-ylcarbonylamino-ethyl)succinamate, MS (ISP): 512 (M+H), are obtained.

5.92 g of the 7.06 g of tert-butyl (S)-2-benzyloxycarbonylamino-N1-cyclopropyl-N1-(2-pyrazin-2-ylcarbonylamino-ethyl)-succinamate are dissolved in 100 ml of hydrochloric acid (in ethyl acetate) and the reaction mixture is stirred at room temperature. After evaporation of the ethyl acetate the residue is dissolved in 70 ml of methylene chloride and 3.96 ml of Hünig's base and 2.52 g of di-tert-butyl dicarbonate are added thereto and the mixture is stirred at room temperature. The mixture is concentrated, the residue is dissolved in 70 ml of methylene chloride and 2.75 g of (S)-1-amidino-3-(aminomethyl)piperidine dihydrochloride, 10.27 ml of Hünig's base and 5.31 g of BOP are added thereto in succession while stirring and the mixture is stirred at room temperature. The evaporation residue is chromatographed over silica gel with ethyl acetate/acetone/water/glacial acetic acid 6:2:1:1. 3.17 g of pure (S)-N4-[(S)-1-(amino-imino-methyl)-piperidin-3-yimethyl]-2-tert-butoxycarbonylamino-N1-cyclopropyl-N1-(2-pyrazin-2-ylcarbonylamino)-succinamide acetate (1:2), MS (ISP): 560.5 (M+H), are obtained.

Preparation of the starting material:

5 g of benzyl 2-cyclopropylamino-ethylcarbamate hydrochloride (1:1) (preparable from Z-glycine and cyclopropylamine via benzyloxycarbonylamino-acetic acid cyclopropylamide) are treated with 4.36 g of di-tert-butyl dicarbonate, 3.08 ml of triethylamine and 100 mg of dimethylaminopyridine at room temperature while stirring. After stirring at room temperature for 20 hours the mixture is taken up in ether and the ether phase is washed with 1N hydrochloric acid and water. The ether phase is concentrated. The oil obtained is dissolved in 100 ml of methanol and treated with 200 mg of Pd/C (10%) and hydrogenated. After filtration of the catalyst the methanol solution is concentrated. A solution of the residue in 100 ml of methylene chloride; is treated with 2.34 g of pyrazinecarboxylic acid, 9.5 ml of Hünig's base and 8.44 g of BOP. After stirring at room temperature the mixture is taken up in ether and the ether phases are washed with water. The residue is chromatographed over silica gel with ethyl acetate-hexane 1:1. The oil obtained is dissolved in 40 ml of ether and treated with 30 ml of 5N hydrochloric acid (in dioxan). After stirring ether is added and the separated crystals are filtered off. 4.1 g of white crystalline cyclopropyl-2-(pyrazin-2-ylcarbonylamino)ethylamine hydrochloride (1:2), MS (EI): 207 (M+H), are obtained.

EXAMPLE 20

300 mg of (S)-N4-[(S)-1-(amino-imino-methyl)-piperidin-3-ylmethyl]-2-tert-butoxycarbonylamino-N1-cyclopropyl-N1-(2-pyrazin-2-ylcarbonylamino)-succinamide acetate (1:2) are dissolved in 2 ml of dioxan and this solution is treated with 5.4 ml of 4N hydrochloric acid is (in dioxan). The mixture is stirred for 2 hours and the dioxan is then evaporated. The residue is placed in 12 ml of methylene chloride and treated while stirring with 76 mg of pyrimidine-2-thioacetic acid, 0.46 ml of Hünig's base and 206 mg of BOP. The mixture is stirred at room temperature and then concentrated. The residue is chromatographed over silica gel with ethyl acetate-acetone-water-glacial acetic acid 4:2:1:1. 167 mg of (S)-N4-[(S)-1-(amino-imino-methyl)-piperidin-3-ylmethyl]-N1-cyclopropyl-N1-(2-pyrazin-2-ylcarbonylamino-ethyl)-2-pyrimidin-2-ylsulphanylacetylamino-succinamide acetate (1:2), MS (ISP): 612.5 (M+H), are obtained.

EXAMPLE 21

The compounds a) (S)-N4-[(S)-1-(amino-imino-methyl)-piperidin-3-ylmethyl]-N1-cyclopropyl-2-(3-indol-3-yl-propionylamino )-N1-(2-pyrazin-2 -ylcarbonylamino-ethyl)-succinamide acetate (1:2), MS (ISP): 631.5 (M+H)

b) methyl (S)-4-[(S)-2-[(S)-1-(amino-imino-methyl)-piperidin-3 -ylmethylcarbonyl]-1-[cyclopropyl-(2-pyrazin-2-ylcarbonylaminoethyl)-carbamoyl]-ethylcarbamoyl]-4-hydroxy-butrate acetate (1:2), MS (ISP): 604.5 (M+H)

c) (S)-2-[(S)-2-acetylamino-3-indol-3-yl-propionylamino]-N4-[(S)-1-(amino-imino-methyl)-piperidin-3-ylmethyl]-N1-cyclopropyl-N1-(2-pyrazin-2-ylcarbonylamino-ethyl)-succinamide acetate (1:2), MS (ISP): 688.6 (M+H)

d) N4-[(S)-1-(amino-imino-methyl)-piperidin-3-ylmethyl]N1-cyclopropyl-2-phenoxyacetylamino-N1-(2-pyrazin-2-ylcarbonylamino-ethyl)-succinamide acetate (1:2), MS (ISP): 594.5 (M+H)

are prepared analogously to Example 20 using the corresponding carboxylic acids in place of pyrimidinethioacetic acid.

EXAMPLE 22

354 mg of tert-butyl (S)-3-[(S)-3-[cyclopropyl-(2-pyrazin-2 -ylcarbonylamino-ethyl)-carbamoyl]-3-(naphthalen-2-ylsulphonylamino)-propionylaminomethyl]-piperidine-1-carboxylate —(prepared from benzyl 2-cyclopropylamine-ethylcarbamate hydrochloride via tert-butyl (S)-3-[(S)-3-[(2-aminoethyl)cyclopropyl-carbamoyl]-3-(naphthalen-2-ylsulphonamino)propionylaminomethyl]-piperidine-1-carboxylate hydrochloride)— are dissolved in 3 ml of methylene chloride and this solution is treated with 5 ml of 5N hydrochloric acid (in dioxan). After stirring for 1 hour this solution is concentrated and the residue is azeotroped with water and then with ethyl acetate. The residue is stirred in 3 ml of methylene chloride and 53 mg of cyanogen bromide are added thereto while cooling with ice and subsequently 0.14 ml of triethylamine in 14 ml of methylene chloride is added dropwise thereto. After stirring at room temperature 70 mg of hydroxylamine hydrochloride and a further 0.14 ml of triethylamine are added. The mixture is stirred for 20 hours, then concentrated and column chromatographed over silica gel with ethyl acetate/acetone/water/glacial acetic acid 6:2:1:1. 60 mg of (S)-N4-[(S)-1-(amino-hydroxyimino-methyl)-piperidin-3-ylmethyl]-N1-cyclopropyl-2-(naphthalen-2-ylsulphonylamino )-N1-[2 -(pyrazin-2-ylcarbonylamino)-ethyl]-succinamide acetate (1:1), MS (ISP): 666.3 (M+H), are obtained.

EXAMPLE 23

1.0 g of benzyl (S)-N1-[3-(benzyloxy-carbonylamino)-ethyl]-N1-cyclopropyl-2-(morpholino-sulphonyl)-aminosuccinamate is dissolved in 10 ml of THF and 3.4 ml of 1N LiOH solution are added. After stirring for 1 hour the solution is treated with 3.4 ml of 1N hydrochloric acid. The solution is subsequently taken up in ethyl acetate and washed with water. After evaporation of the ethyl acetate there are obtained 997 mg of free acid which, dissolved in 10 ml of methylene chloride, is is subsequently treated with 1 ml of N-ethylmorpholine, 360 mg of (S)-1-amidino-3-(aminomethyl)piperidine dihydrochloride and 715 mg of BOP. The mixture is stirred at room temperature and subsequently concentrated. The residue is chromatographed over silica gel with ethyl acetate/acetone/water/glacial acetic acid 6:2:1:1 and 740 mg of benzyl 2-[[(S)-3-[(S)-1-(amino-imino-methyl)-piperidin-3-ylmethylcarbamoyl]-2-morpholin-4-ylsulphonylamino-propionyl]cyclopropyl-amino]-ethylcarbamate, MS (ISP): 637.5 (M+H), are obtained.

Preparation of the starting material:

5.0 g of benzyl 2-cyclopropylamino-ethylcarbamate hydrochloride (1:1), 5.97 g of BOC-Asp(OBzl)—OH and 7.16 g of Hünig's base are placed in 120 ml of methylene chloride and this solution is treated with 8.57 g of BOP. After stirring at room temperature for 2 hours the solution is taken up in ether and the ether phases are washed with 1N hydrochloric acid, water, bicarbonate solution and again with water. The evaporation residue is chromatographed over silica gel with ethyl acetate/hexane 1:2. 1.76 g of the 9.6 g of intermediate, which is obtained from chromatography, are dissolved in 19 ml of THF and this solution is treated with 6 ml of 4N hydrochloric acid (in dioxan). After stirring at room temperature the mixture is evaporated. 1.54 g of the 2.29 g of oil obtained are dissolved in 18 ml of methylene choride and 1.2 g of morpholine N-sulphochloride and 2.2 ml of Hünig's base are added thereto. The mixture is stirred for 20 hours, taken up in ethyl acetate and washed with 1N hydrochloric acid and water. After drying and evaporation the residue is column chromatographed over silica gel with ethyl acetate/hexane 1:1. 920 mg of benzyl (S)-N1-[3 -(benzyloxy-carbonylamino)-ethyl]-N1-cyclopropyl-2 -(morpholinosulphonyl)-amino-succinamate, MS (FAB): 589.1 (M+H), are obtained.

EXAMPLE 24

325 mg of benzyl 2-[[(S)-3-[(S)-1-(amino-imino-methyl)-piperidin-3-ylmethylcarbamoyl]-2-morpholin-4-ylsulphonylaminopropionyl]-cyclopropyl-amino]-ethylcarbamate are dissolved in 10 ml of methanol. After the addition of 35 mg of Pd/C (10%) the mixture is hydrogenated at room temperature and the catalyst is subsequently filtered off. After evaporation the residue is dissolved in 4 ml of methylene chloride and 48 mg of pyrazinecarboxylic acid, 0.24 ml of N-ethylmorpholine and 178 mg of BOP are added thereto while stirring. After stirring at room temperature the mixture is concentrated and the residue is chromatographed over silica gel with ethyl acetate/acetone/water/glacial acetic acid 6:2:1:1. 181 mg of (S)-N4-[(S)-1-(amino-imino-methyl)-piperidin-3-ylmethyl]-N1-cyclopropyl-2-morpholin-4-ylsulphonylamino-N1-(2-pyrazin-2-ylcarbonylaminoethyl)-succinamide acetate (1:1), MS (ISP): 609.5 (M+H), are obtained.

EXAMPLE 25

When 2,3-dihydro-3-oxopyridazine-6-carboxylic acid is used in place of the pyrazinecarboxylic acid used in Example 24, there is obtained (S)-N4-[(S)-1-(amino-iminomethyl)-piperidin-3-ylmethyl]-N1-cyclopropyl-2-morpholin-4-ylsulphonylamino-N1-[2-(6-oxo-1,6 -dihydro-pyridazin-3-ylcarbonylamino-ethyl]-succinamide acetate (1:1), MS (ISP): 625.4 (M+H).

EXAMPLE 26

When the following acids are used in place of the pyrazinecarboxylic acid used in Example 24:
 a) 6-oxo-1,4,5,6-tetrahydro-pyridazinecarboxylic acid,
 b) 3-amino-pyrazine-2-carboxylic acid,
 c) methoxy-acetic acid,
 d) morpholino-acetic acid,
 e) 4-methyl-piperazine-1-acetic acid,
 f) 3-methoxy-propionic acid,
 g) 1-imidazolyl-acetic acid or
 h) 2-hydroxyamino-glutaric acid,
then the following products are obtained:
 a) (S)-N4-[(S)-1-(amino-imino-methyl)-piperidin-3-ylmethyl]-N1-cyclopropyl-2-morpholin-4-ylsulphonylamino-N1-[2-(6-oxo-1,4,5,6 -tetrahydro-pyridazin-3-ylcarbonylamino)-ethyl]-succinamide acetate (1:1), MS (ISP): 627.6 (M+H),
 b) (S)-N4-[(S)-1-(amino-imino-methyl)-piperidin-3-ylmethyl]-N1-[2-(3-amino-pyrazin-2-ylcarbonylamino) -ethyl]-N1-cyclopropyl-2-morpholin-4-ylsulphonylamino-succinamide acetate (1:1), MS (ISP): 624.6 (M+H),
 c) (S)-N4-[(S)-1-(amino-imino-methyl)-piperidin-3-ylmethyl]-N-1-cyclopropyl-N1-(2-methoxyacetylaminoethyl)-2-morpholin-4 -ylsulphonylamino-succinamide acetate (1:1), MS (ISP): 575,5 (M+H),
 d) (S)-N4-[(S)-1-(amino-imino-methyl)-piperidin-3-ylmethyl]-N-1 -cyclopropyl-N1-(2-morpholin-4-ylacetylamino-ethyl)-2-morpholin-4 -ylsulphonylamino-succinamide acetate (1:1), MS (ISP): 630.6 (M+H) and 316.2 (M+2H),
 e) (S)-N4-[(S)-1-(amino-imino-methyl)-piperidin-3-ylmethyl]-N1-cyclopropyl-N1-[2-(4-methyl-piperazin-1-ylacetylamino)-ethyl]-2-morpholin-4-ylsulphonylamino-succinamide acetate (1:1), MS (ISP): 643.6 (M+H),
 f) (S)-N4-[(S)-1-(amino-imino-methyl)-piperidin-3-ylmethyl-N1-cyclopropyl-N1-[2-(3-methoxy-propionylamino)-ethyl]-2-morpholin-4 -ylsulphonylamino-succinamide acetate (1:1), MS (ISP): 589.6 (M+H),
 g) (S)-N4-[(S)-1-(amino-imino-methyl)-piperidin-3-ylmethyl]-N1-cyclopropyl-N1-(2-imidazol-1-ylacetylamino-ethyl)-2-morpholin-4 -ylsulphonylamino-succinamide acetate (1:1), MS (ISP): 611.6 (M),
 h) (E)- and (Z)-4-[2-[[(S)-3-[(S)-1-(amino-imino-methyl)-piperidin-3-ylmethylcarbamoyl]-2-morpholin-4-ylsulphonylamino-propionyl]cyclopropyl-amino]-ethylcarbamoyl]-4-hydroxyimino-butyric acid acetate (1:1), MS (ISP): 646.5 (M+H).

EXAMPLE 27

2.77 g of benzyl 2-[[(S)-3-[(S)-1-(amino-imino-methyl)-piperidin-3-ylmethyl-carbamoyl]-2-morpholin-4-ylsulphonylamino-propionyl]-cyclopropyl-amino]-ethylcarbamate (Example 23) are dissolved in 90 ml of methanol. After the addition of 2.13 ml of 2N hydrochloric acid and 300 mg of Pd/C (10%) the mixture is hydrogenated at room temperature for 1.5 hours, the catalyst is then filtered off and the filtrate is evaporated. The residue is dispersed with ether and the white crystals are filtered off. 2.44 g of crystalline (S)-N1-(2-amino-ethyl)-N4-[(S)-1-(amino-imino-methyl)-piperidin-3-ylmethyl]-N1-cyclopropyl-2-morpholin-4 -ylsulphonylamino-succinamide hydrochloride (1:2), MS (ISP): 503.4 (M+H), are obtained.

EXAMPLE 28

330 mg of (S)-N1-(2-amino-ethyl)-N4-[(S)-1-(aminoimino-methyl)-piperidin-3-ylmethyl]-N1-cyclopropyl-2-morpholin-4 -ylsulphonylamino-succinamide hydrochloride are stirred at room temperature for 20 hours together with 162 mg of 4-methyl-piperazin-1-ylsulphonyl chloride and 0.49 ml of Hünig's base in 8 ml of methylene chloride. The reaction mixture is chromatographed over silica gel with ethyl acetate/acetone/glacial acetic acid/water 2:2:2:1. 14.9.1 mg of pure crystalline (S)-N4-[(S)-1-(amino-iminomethyl)-piperidin-3-ylmethyl]-N1-cyclopropyl-N1-[2-(4-methyl-piperazin-1-ylsulphonylamino)-ethyl]-2-morpholin-4 -ylsulphonylamino-succinamide acetate (1:2), MS (ISP): 665.6 (M+H) and 333.7 (M+2H), are obtained.

EXAMPLE 29

(S)-N4-[(S)-1-(Amino-imino-methyl)-piperidin-3-ylmethyl-N1-cyclopropyl-2-morpholin-4-ylsulphonylamino-N1-(2-morpholin-4 -ylsulphonylamino-ethyl)-succinamide acetate (1:1), MS (ISP): 652.5 (M+H), is obtained analogously to Example 28 using morpholinosulphonyl chloride in place of 4-methyl-piperazin-1-ylsulphonyl chloride.

EXAMPLE 30

Analogously to Example 20, but using the carboxylic acids:
 a) 3-methoxy-propionic acid,
 b) morpholinoacetic acid,
 c) methoxyacetic acid,
 d) 4-methyl-piperazine-1-acetic acid,
 e) (L)-phenylalanine,
 f) (D)-phenylalanine,
 g) 4-hydroxy-piperidine-1-acetic acid,
 h) 1-imidazolyl-acetic acid,
 i) 2-piperidone-1-acetic acid,
 j) 3-dimethylamino-propionic acid,
 k) dimethylamino-acetic acid and, respectively,
 l) 2,6-dimethylmorpholine-4-acetic acid
in place of pyrimidinethioacetic acid the following compounds are prepared:
 a) (S)-N4-[(S)-1-(amino-imino-methyl)-piperidin-3-ylmethyl]-N1-cyclopropyl-2-(3-methoxy-propionylamino)-N1-(2-pyrazin-2 -ylcarbonylamino-ethyl)-succinamide acetate (1:2), MS (ISP): 546.5 (M+H),
 b) (S)-N4-[(S)-1-(amino-imino-methyl)-piperidin-3-ylmethyl]-N1-cyclopropyl-2-morpholin-4-ylacetylamino-N1-(2-pyrazin-2 -ylcarbonylamino-ethyl)-succinamide acetate (1:3), MS (EI): 587.3 (M+H),
 c) (S)-N4-[(S)-1-(amino-imino-methyl)-piperidin-3-ylmethyl]-N1-cyclopropyl-2-methoxyacetylamino-N1-(2- pyrazin-2-ylcarbonylaminoethyl)-succinamide acetate (1:2), MS (ISP): 532.6 (M+H), d) (S)-N4-[(S)-1-(amino-imino-methyl)-piperidin-3-ylmethyl]-N1-cyclopropyl-2-(4-methyl-piperazin-1-ylacetylamino )-N1-(2-pyrazin-2-ylcarbonylaminoethyl)-succinamide acetate (1:3), MS (ISP): 600.6 (M+H), e) (S)-N4-[(S)-1-(amino-imino-methyl)-piperidin-3-ylmethyl]-2-[(S)-2-amino-3-phenyl-propionylamino]-N1-cyclopropyl-N1-(2-pyrazin-2-ylcarbonylaminoethyl)-succinamide hydrochloride (1:2), MS (ISP): 607.5 (M+H), f) (S)-N4-[(S)-1-(amino-imino-methyl)-piperidin-3-ylmethyl-2-[(R)-2-amino-3-phenyl-propionylamino]-N1-cyclopropyI-N1-(2-pyrazin-2-ylcarbonylamino-ethyl)-succinamide hydrochloride (1:2), MS (ISP): 607.5 (M+H) and 304.6 (M+2H), g) (S)-N4-[(S)-1-(amino-imino-methyl)-piperidin-3-ylmethyl]-N1-cyclopropyl-2-[2-(4-hydroxy-piperidin-1-yl)-acetylamino]-N1-(2-pyrazin-2-ylcarbonylaminoethyl)-succinamide hydrochloride (1:2), MS (ISP): 601.6 (M+H), h) (S)-N4-[(S)-1-(amino-imino-methyl)-piperidin-3-ylmethyl]-N1-cyclopropyl-2-(2-imidazol-1-yl-acetylamino)-N1-(2-pyrazin-2 -ylcarbonylamino-ethyl)-succinamide hydrochloride (1:2), MS (ISP): 568.5 (M+H), i) (S)-N4-[(S)-1-(amino-imino-methyl)-piperidin-3-ylmethyl]-N1-cyclopropyl-2-[2-(2-oxo-piperidin-1-yl)-acetylamino]-N1-(2-pyrazin-2-ylcarbonylaminoethyl)-succinamide hydrochloride (1:2), MS (ISP): 599.5 (M+H), j) (S)-N4-[(S)-1-(amino-imino-methyl)-piperidin-3-ylmethyl]-N1-cyclopropyl-2-(3-dimethylamino-propionylamino )-N1-(2-pyrazin-2 -ylcarbonylamino-ethyl)-succinamide hydrochloride (1:3), MS (ISP): 559.6 (M+H), k) (S)-N4-[(S)-1-(amino-imino-methyl)-piperidin-3-ylmethyl]-N1-cyclopropyl-2-(2-dimethylamino-acetylamino)-N1-(2-pyrazin-2-ylcarbonylamino-ethyl)-succinamide hydrochloride (1:3), MS (ISP): 545.6 (M+H), l) (S)-N4-[(S)-1-(amino-imino-methyl)-piperidin-3-ylmethyl]-N1-cyclopropyl-2-(2,6-dimethyl-morpholin-4-ylacetylamino)-N1-(2-pyrazin- 2-ylcarbonylaminoethyl)-succinamide hydrochloride (1:2) (R:S =1:1 for C2 and C6 in the morpholino ring), MS: 615.4 (M+H).

EXAMPLE 31

A solution of 3.0 g of the product of Example 7.B)a) in 63 ml of ethanol and 7 ml of water is treated with 0.95 ml of cinnamaldehyde and 1.6 ml of 4-ethylmorpholine and stirred at room temperature for 20 minutes. 0.3 g of Pd/C catalyst is added to this solution and the reaction mixture is hydrogenated under normal conditions for 6 hours. Then, the catalyst is filtered off, the filtrate is evaporated and the residue is chromatographed on RP-18 with a water-acetonitrile gradient. The product fractions are evaporated and filtered over an ion exchanger (Cl- form) with water-ethanol. Colourless ethyl 3-[[(S)-3-[(S)-1-(amino-imino-methyl)-piperidin-3-ylmethylcarbamoyl]-2-(3 -phenyl-propylamino) propionyl]-cyclopropyl-amino]-propionate hydrochloride (1:2), MS (ion spray): 529.6 (M+H)$^+$, is isolated after evaporation.

EXAMPLE 32

The following product is prepared analogously to Example 31:

Ethyl 3-[[(S)-3-[(S)-1-(amino-imino-methyl)-piperidin-3-ylmethylcarbamoyl]-2-butylamino-propionyl]-cyclopropyl-amino]propionate hydrochloride (1:2), MS (ion spray): 467.6 (M+H)$^+$.

EXAMPLE 33

The following products are obtained analogously to Example 3, but with an additional filtration of the end product over an ion exchanger (Cl- form) with water-ethanol:

a) 3-[[(S)-3-[(S)-1-(Amino-imino-methyl)-piperidin-3-ylmethylcarbamoyl]-2-(3-phenyl-propylamino)-propionyl]-cyclopropylamino]-propionic acid hydrochloride (1:1), MS (ion spray): 501.7 (M+H)$^+$, b) 3-[[(S)-3-[(S)-1-(amino-imino-methyl)-piperidin-3-ylmethylcarbamoyl]-2-butylamino-propionyl]-cyclopropyloamino]propionic acid hydrochloride (1:1), MS (ion-spray): 439.6 (M+H)$^+$.

EXAMPLE 34

0.34 g of palladium/charcoal catalyst is added to a solution of 3.4 g of the product of Example 3 in 34 ml of ethanol and 6.8 ml of 1N hydrochloric acid and the reaction mixture is hydrogenated for 2 hours. Then, the catalyst is filtered off and the filtrate is evaporated. Colourless [[(S)-2-amino-3-[(S)-1-(amino-imino-methyl)-piperidin-3-ylmethylcarbamoyl]-propionyl]-cyclopropyl-amino]-acetic acid hydrochloride (1:1), MS (ion spray): 369.4 (M+H)$^+$, is thus isolated.

EXAMPLE 35

The following compound is prepared from the product of Example 37 analogously to Example 34:

(S)-3-Amino-N-[(S)-1-(amino-imino-methyl)-piperidin-3-ylmethyl]-4-azepan-1-yl-4-oxo-butyramide hydrochloride (1:2), MS (ion spray): 353.4 (M+H)$^+$.

EXAMPLE 36

2.1 g of the product of Example 7.A) are dissolved in 45 ml of ethanol and 5 ml of water, treated with 0.7 g of cinnamaldehyde and 1.1 ml of 4oethylmorpholine and stirred at room temperature for 15 minutes. Then, 0.2 g of Pd/C catalyst is added and the mixture is hydrogenated under normal conditions for 6 hours. The catalyst is filtered off, the filtrate is evaporated and the residue is chromatographed on RP-18 with a water-acetonitrile gradient. The product fractions are evaporated and the residue is filtered over an ion exchanger (Dowex, Cl- form). 0.5 g of N-[(S)-1-(amino-imino-methyl)piperidine-3oylmethyl]-2-[(S)-4-cyclopropyl-3,6-dioxo-1-(3-phenylpropyl)-piperazin- 2-yl]-acetamide hydrochloride (1:1), MS (ISP): 469.5 (M+H)$^+$, is isolated after evaporation.

EXAMPLE 37

The following compound is prepared analogously to Example 1:

(S)-N-[(S)-1-(Amino-imino-methyl)-piperidin-3-ylmethyl]-4-azepan-1-yl-3-benzyloxycarbonylamino-4-oxo-butyramide hydrochloride (1:1), MS (ion spray): 487.5 (M+H)$^+$.

Preparation of the starting material:

The following intermediate is prepared analogously to Example 1.B), but using hexamethyleneimine in place of N-cyclopropylglycine ethyl ester:

t-Butyl (S)-4-azepan-1-yl-3-benzyloxycarbonylamino-4-oxo-butyrate, MS (ion spray): 405.2 (M+H)⁺.

EXAMPLE 38

The following compounds are prepared analogously to Example 9, but using the corresponding activated carbamates:

a) Ethyl [[(S)-3-[(S)-1-(amino-imino-methyl)-piperidin-3-ylmethylcarbamoyl]-2-(3-diphenylmethyl-ureido) -propionyl]cyclopropyl-amino]-acetate hydrochloride (1:1), MS (ion spray): 606,-.6 (M+H)⁺, b) ethyl [[(S)-3-[(S)-1-(amino-imino-methyl)-piperidin-3-ylmethylcarbamoyl]-2-(3-cyclohexylmethyl-ureido)-propionyl]cyclopropyl-amino]-acetate hydrochloride (1:1), MS (ion spray): 536,5 (M+H)⁺.

Preparation of the starting materials:

The following activated carbamates are prepared analogously to Example 9.B)b:

2,5-Dioxo-pyrrolidin-1-yl diphenylmethyl-carbamate, MS (FAB): 209 (M-hydroxysuccinimide), 2,5-dioxo-pyrrolidin-1-yl cyclohexylmethylcarbamate, MS (FAB): 115 (M-hydroxysuccinimide).

EXAMPLE 39

The following compounds are prepared analogously to Example 9, but starting from the amine of Example 35 and using the corresponding activated carbamates:

a) (S)-N-[(S)-1-(Amino-imino-methyl)-piperidin-3-ylmethyl]-4-azepan-1-yl-3-(3-benzyl-ureido)-4-oxo-butyramide hydrochloride (1:1), MS (ion spray): 486.4 (M+H)⁺, b) methyl (S)-2-[3-[(S)-1-[(S)-(amino-imino-methyl)-piperidin-3-ylmethylcarbamoylmethyl]-2-azepan-1-yl-2-oxo-ethyl]-ureido]-3-phenylpropionate hydrochloride (1:1), MS (ion spray): 558.5 (M+H)⁺, c) methyl (R)-2-[3-[(S)-1-[(S)-(amino-imino-methyl)-piperidin-3-ylmethylcarbamoylmethyl]-2-azepan-1-yl-2-oxo-ethyl]-ureido]-3-phenylpropionate hydrochloride (1:1), MS (ion spray): 558.5 (M+H)⁺.

Preparation of the starting materials:

The following activated carbamates are prepared analogously to Example 9.B)b):

2,5-Dioxo-pyrrolidin-1-yl benzylcarbamate MS (FAB): 133 (M-hydroxysuccinimide), methyl (R)-2-(2,5-dioxo-pyrrolidin-1-yloxycarbonylamino)-3-phenylpropionate, MS (FAB): 133 (M-hydroxysuccinimide), methyl (S)-2-(2,5-dioxo-pyrrolidin-1-yloxycarbonylamino)-3-phenylpropionate, MS (FAB): 162 (M-H₂NCOO-succinimide).

EXAMPLE 40

The following products are prepared analogously to Example 3, but using the products of Examples 38 and 39b) and c):

a) [[(S)-3-[(S)-1-(Amino-imino-methyl)-piperidin-3-ylmethylcarbamoyl]-2-(3-diphenylmethyl-ureido)-propionyl]cyclopropyl-amino]-acetic acid, MS (ion spray): 578.3 (M+H)⁺, b) [[(S)-3-[(S)-1-(amino-imino-methyl)-piperidin-3-ylmethylcarbamoylmethyl]-2-(3-cyclohexylmethyl-ureido)-propionyl]cycolpropyl-amino]-acetic acid, MS (ion spray): 508.5 (M+H)⁺, c) (S)-2-[3-[(S)-1-[(S)-(amino-imino-methyl)-piperidin-3-ylmethylcarbamoylmethyl]-2-azepan-1-yl-2-oxo-ethyl]-ureido]-3-phenylpropionic acid, MS (ion spray): 544.5 (M+H)⁺, d) (R)-2-[3-[(S)-1-[(S)-(amino-imino-methyi)-piperidin-3-ylmethylcarbamoylmethyl]-2-azepan-1-yl-2-oxo-ethyl]-ureido]-3-phenylpropionic acid, MS (ion spray): 544.6 (M+H)⁺.

EXAMPLE 41

[[(S)-2-Benzyloxycarbonylamino-3-[(S)-1-(ethoxycarbonylamino-imino-methyl)-piperidin-3-ylmethylcarbamoyl]-propionyl]cyclopropyl-amino]-acetic acid, MS (ion spray): 575.5 (M+H)⁺, is obtained analogously to Example 1, but using ethyl (S)-(3-aminomethyl-piperidin-1-yl)-imino-methylcarbamate hydrochloride in place of (S)-1-amidino-3-(aminomethyl)piperidine dihydrochloride.

EXAMPLE 42

[[(S)-2-Benzyloxycarbonylamino-3-[4-(ethoxycarbonylamino-imino-methyl)-morpholin-2-ylmethylcarbamoyl]-propionyl]cyclopropyl-amino]-acetic acid (R:S=1:1 in the morpholine ring), MS (ion spray): 577.5 (M+H)⁺, is obtained analogously to Example 41, but using ethyl (RS)-(2-aminomethyl-morpholin-4-yl)-imino-methylcarbamate hydrochloride in place of ethyl (S)-(3-aminomethyl-piperidine-1-yl)-imino-methylcarbamate hydrochloride.

EXAMPLE 43

Analogously to Example 15, but starting from a) [(S)-3-[(S)-1-(amino-imino-methyl)-piperidin-3-ylmethylcarbamoyl]-2-naphthalen-2-yl-sulphonylamino-propionylamino]-acetic acid and, respectively, b) (S)-2-[(S)-3-[(S)-1-(amino-imino-methyl)-piperidin-3-ylmethylcarbamoyl]-2-naphthalen-2-yl-sulphonylamino-propionylamino]3-hydroxy-propionic acid the following products are prepared:

a) N-[(S)-1-(amino-imino-methyl)-piperidin-3-ylmethyl] -2-[(S)-1-napthalen-2-ylsulphonyl-3,6-dioxo-piperazin-2-yl]-acetamide hydrochloride (1:1), MS (ion spray): 501.4 (M+H)⁺, b) N-[(S)-1-(amino-imino-methyl)-piperidin-3-ylmethyl] -2-[(2S,5S)-5-hydroxymethyl-1-naphthalen-2-ylsulphonyl-3,6-dioxo-piperazin-2-yl]-acetamide hydrochloride (1:1), MS (ion spray): 531.4 (M+H)⁺.

Preparation of the starting materials:

1. Starting from N-Boc-L-aspartic acid β-t-butyl ester and from glycine ethyl ester or serine methyl ester there is obtained via 1.a) t-butyl-(S)-3-(1-t-butoxyformamido)-N-[(ethoxycarbonyl)methyl]succinamate or 1.b) t-butyl-(S)-3-(1-t-butoxyformamido)-N-[1-(2-hydroxy-1 -methoxycarbonyl)-ethyl]succinamate, via 2.a) t-butyl-(S)-N-[(ethoxycarbonyl)methyl]-3-(naphthalen-2-ylsulphonamido)succinamate or 2.b) t-butyl-(S)-N-[1-(2-hydroxy-1-methoxycarbonyl)-ethyl]-3-(naphthalen- 2-ylsulphonamido)succinamate and via 3.a) ethyl [(S)-3-[(S)-1-(amino-imino-methyl)-piperidin-3-ylmethylcarbamoyl]-2-naphthalen-2-yl-sulphonylamino-propionylamino-acetate hydrochloride (1:1), MS (ISP): 547.4 (M+H)⁺, or 3.b) methyl (S)-2-[(S)-3-[(S)-1-(amino-imino-methyl)-piperidin-3-ylmethylcarbamoyl]-2-naphthalen-2-yisulphonylamino-propionylamino]-3-hydroxy-propionate hydrochloride (1:1), MS (ISP): 563.4 (M+H)$^+$, 4.a) [(S)-3-[(S)-1-(amino-imino-methyl)-piperidin-3-yl-methylcarbamoyl]-2-naphthalen-2-ylsulphonylamino-propionylamino]-acetic acid, MS (ISP): 519.4 (M+H)$^+$, and, respectively, 4.b) (S)-2-[(S)-3-[(S)-1-(amino-imino-methyl)-piperidin-3-ylmethylcarbamoyl]-2-naphthalen-2-ylsulphonylamino-propionylamino]-3-hydroxypropionic acid, MS (ISP): 549.3 (M+H)$^+$.

EXAMPLE 44

A (1:1) mixture of (2S,5R)- and (2S,5S)-(5-benzyl-3,6-dioxo-4-propyl-piperazin-2-yl)-acetic acid (S)-1-(amino-imino-methyl)-piperidine-3-yimethylamide hydrochloride (1:1), MS (ion spray): 443.6 (M+H)$^+$, is obtained analogously to Example 1.A) from a (1:1) mixture of t-butyl (2S,5R)- and (2S,5S)-(5-benzyl-3,6-dioxo-4-propyl-piperazin-2-yl)-acetate.
Preparation of the starting material:
The t-butyl (2S,5R)- and (2S,5S)-(5-benzyl-3,6-dioxo-4-propyl-piperazin-2-yl)-acetate, MS (FaB): 360 (M$^+$), is obtained starting from N-Boc-L-aspartic acid β-t-butyl ester and rac-N-propyl-phenylalanine methyl ester via t-butyl (S)-2-t-butoxycarbonylamino-N-[(R)- and [(S)-1-methoxycarbonyl-2-phenyl-ethyl]-N-propyl-succinamate, MS (ISP): 493.5 (M+H)$^+$.

EXAMPLE 45

Ethyl (S)-[2-[(S)-1-(amino-imino-methyl)-piperidin-3-ylmethylcarbamoylmethyl]-4-cyclopropyl-3,6-dioxo-piperazin-1-yl]-acetate hydrochloride (1;1), MS (ion spray): 437.5 (M+H)$^+$, is obtained analogously to Example 1.A) from t-butyl (S)-(4-cyclopropyl-1-ethoxycarbonylmethyl-3,6-dioxo-piperazin-2-yl)-acetate.
Preparation of the starting material:
a) 0.67 g of the product of Example 7.A) are dissolved in 7 ml of DMF, treated with 0.5 ml of 4-ethylmorpholine and stirred at 80° C. overnight. The reaction mixture is evaporated and the residue is chromatographed on silica gel with ethyl acetate-methanol (99:1). 0.43g of colourless t-butyl (S)-(4-cyclopropyl-3,6-dioxo-piperazin-2-yl)-acetate, MS (ion spray): 269.3 (M+H)$^+$, is thus obtained.

b) 1.9 g of sodium hydride dispersion (80%) are added to a solution of 3.45 g of the product obtained under a) in 50 ml of DMF and subsequently 7.1 ml of ethyl bromoacetate are added dropwise at 3°–10° C. The reaction mixture is stirred at room temperature for 4 hour, then poured into water and extracted with ethyl acetate. The organic phase is washed with sodium chloride solution, dried and evaporated. After chromatography of the residue on silica gel with ethyl acetate-hexane (1:1) there are obtained 1.6g of t-butyl (S)-(4-cyclopropyl-1-ethoxycarbonylmethyl-3,6-dioxo-piperazin-2-yl)-acetate in the form of a yellow resin, MS (ion spray): 355.4 (M+H)$^+$.

EXAMPLE 46

[(S)-2-[(S)-1-(Amino-imino-methyl)-piperidin-3-ylmethylcarbamoylmethyl]-4-cyclopropyl-3,6-dioxo-piperazin-1-yl]-acetic acid, MS (ion spray): 409.5 (M+H)$^+$, is obtained from the product of Example 45 analogously to Example 3.

EXAMPLE 47

A solution of 6.5g of (RS)-(2,4-dimethyl-1-naphthalen-2-ylsulphonyl-3-oxo-piperazin-2-yl)-acetic acid in 65 ml of DMF is treated in succession with 7.64 g of BOP, 6.5 ml of 4-ethylmorpholine and 4.35g of (S)-1-amidino-3-(aminomethyl)-piperidine dihydrochloride and stirred at room temperature overnight. After evaporation of the solvent the residue is chromatographed on RP-18 with a water-acetonitrile gradient. The product fractions are evaporated and the residue is filtered over an ion exchanger (Dowex, Cl- form). A (1:1) mixture of (R)- and (S)-(2,4-dimethyl-1-naphthalen-2-ylsulphonyl-3-oxo-piperazin-2-yl)-acetic acid (S)-1-(amino-imino-methyl)-piperidin-3-ylmethylamide hydrochloride (1:1), MS (ion spray): 515.6 (M+H)$^+$, is isolated after evaporation.
Preparation of the starting material:
a) A solution of 10 g of ethyl-2-pyrazin-3-one-acetate in 100 ml of dioxan is treated with 6.8 ml of 4-ethylmorpholine and a solution of 12.9 g of di-tert-butyl dicarbonate in 50 ml of dioxan and stirred at room temperature for 6 hours. The solvent is evaporated and the residue is purified on silica gel with ethyl acetate-hexane (1:1). 15.4g of t-butyl (RS)-2-ethoxycarbonylmethyl-3-oxo-piperazine-1-carboxylate, MS (ion spray): 287.3 (M+H)$^+$, is obtained.

b) A solution of 15.0 g of the compound obtained under a) in 200 ml of DMF is treated with 7.9 g of sodium hydride dispersion (80%). Subsequently, 16.3 ml of methyl iodide are added dropwise at 3°–10° C., the reaction mixture is stirred at room temperature for 4 hours, then poured into water and extracted with ethyl acetate. The organic phase is washed with water, dried and evaporated. The residue is chromatographed on silica gel with ethyl acetate-hexane (1:1). 11.4g of t-butyl (RS)-2-ethoxycarbonylmethyl-2,4-dimethyl-3-oxo-piperazine- 1-carboxylate, MS (FAB): 314 (M$^+$), are obtained.

c) A solution of the product of b) in acetonitrile is treated with p-toluenesulphonic acid monohydrate. After evaporation a solution of the residue in dioxan is treated with ⊖-naphthyl sulphochloride. Ethyl (RS)-(2,4-dimethyl-1-naphthalen-2-ylsulphonyl-3-oxo-piperazin-2-yl)-acetate, MS (FAB): 405 (M+H)$^+$, is obtained.

d) (RS)-(2,4-ddmethyl-1-naphthalen-2-ylsulphonyl-3-oxo-piperazin-2-yl)-acetic acid, MS (ion spray): 375.4 (M-H)-, is obtained from the product of c) analogously to Example 3.

EXAMPLE 48

2.35 g of the amine product of Example 7.A) in 25 ml of DMF are treated with 3.2 ml of 4-ethylmorpholine and 0.5 ml of chloroacetyl chloride and stirred at room temperature overnight. The reaction mixture is evaporated and the residue is chromatographed on a RP-18 column with a water-acetonitrile gradient. 0.5 g of ethyl [[(S)-3-[(S)-1-amino-imino-methyl)-piperidin-3-ylmethylcarbamoyl]-2-(2-chloro-acetylamino)-propionyl]-cyclopropyl-amino]-acetate hydrochloride (1:1), MS (ISP): 473.4 (M+H)$^+$, is obtained from the product fractions after evaporation.

EXAMPLE 49

[[(S)-3-[(S)-1-Amino-imino-methyl)-piperidin-3-ylmethylcarbamoyl]-2-(2-chloro-acetylamino)-propionyl]-cyclopropyl-amino]acetic acid, MS (ISP): 445.4 (M+H)$^+$, is obtained from the product of Example 48 analogously to Example 3.

EXAMPLE 50

0.9 g of the amine product of 7.A) and 0.5 g of sodium hydrogen carbonate are dissolved in 9 ml of THF and 9 ml of water, treated with 0.82 g of morpholine N-sulphochloride in 8 ml of THF and 1.9 ml of 1N sodium hydroxide solution and stirred at room temperature for 48 hours. The reaction mixture is made acid with 1N hydrochloric acid, evaporated and the residue is chromatographed on a RP-18 column with a water-acetonitrile gradient. 0.2 g of colourless ethyl 3-[[(S)-3-[(S)-1-(amino-imino-methyl)-piperidin-3-ylmethylcarbamoyl]-2-morpholin-4-ylsulphonylamino-propionyl]-cyclopropyl-amino]propionate hydrochloride (1:1), MS (ISP): 560.5 (M+H)$^+$, is obtained from the product fractions after evaporation.

EXAMPLE 51

3-[[(S)-3-[(S)-1-(Amino-imino-methyl)-piperidin-3-ylmethylcarbamoyl]-2-morpholin-4-ylsulphonylamino-propionyl]-cyclopropyl-amino]-propionic acid, MS (ion spray): 532.5 (M+H)$^+$, is obtained from the product of Example 50 analogously to Example 3.

A compound of formula I, a solvate or salt thereof can be used in a manner known per se as the active ingredient for the production of pharmaceutical preparations, e.g. of tablets and capsules of the following composition:

Example A

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

|  | Per capsule |
| --- | --- |
| Active ingredient | 100.0 mg |
| Corn starch | 20.0 mg |
| Lactose | 95.0 mg |
| Talc | 4.5 mg |
| Magensium stearate | 0.5 mg |
|  | 220.0 mg |

We claim:

1. Carboxamides of the formula

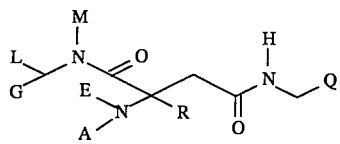

wherein

E is hydrogen,

G is H, lower-alkyl or (optionally bonded via lower-alkylene) COOH, COO-lower-alkyl, lower-alkanoyl, OH, lower-alkanoyloxy, lower-alkoxy, aryl-lower-alkoxy, $CONH_2$, $CONHCH_2CH_2OH$, CONHOH, $CONHOCH_3$, CONHO-benzyl, $CONHSO_2$-lower-alkyl, $CONHCH_2CH_2$-aryl, CONH-cycloalkyl, CONHCH$_2$-heteroaryl, $NH_2$, NHCOO-lower-alkyl, NHCOO-lower-aralkyl, $NHSO_3H$, ($NHSO_2$ or $NHSO_3$)-lower-alkyl, NH lower-alkanoyl, NHCOCOOH, NHCOCOO-lower-alkyl, NH-cycloalkyl, NH-(3,4-dioxo-2-hydroxy-cyclobut-1-enyl), NH-[2-lower-(alkoxy or -alkenyloxy)-3,4-dioxocyclobut-1-enyl]], NHCH$_2$-heteroaryl, NHCOCO-(aryl or lower-alkyl), NHCOCH$_2$Cl, NHCO-lower-alkylene-O-(lower-alkyl or aryl), NHCOCH$_2$[aryl, heteroaryl or —N(Het)], NHCOC(NOH)-lower-alkylene-COOH, NHSO$_2$-N(Het), NHCO-(aryl, heteroaryl or heterocyclyl), NHPO$_3$(R$^{10}$,R$^{20}$), heteroaryl or a group CO—N(Het), R$^{10}$ and R$^{20}$ are H, lower-alkyl or phenyl, M is H, lower-alkyl or -alkenyl, aryl, heteroaryl, cycloalkyl or (aryl, heteroaryl or cycloalkyl)-lower-alkyl and L is H, lower-alkyl, aryl, cycloalkyl or (aryl or cycloalkyl)-lower-alkyl or M and L together with the atoms to which they are attached form a group —N(Het) or E and G together form a methylene or carbonyl group and M is H, lower-alkyl or-alkenyl, aryl, heteroaryl, cycloalkyl, (aryl, heteroaryl or cycloalkyl)-lower-alkyl or carboxy-lower-alkyl and L is H, lower-alkyl, aryl, cycloalkyl or (aryl or cycloalkyl)-lower-alkyl, A is H, alkyl, lower-aralkyl or a group of the formula:

or, where group Q contains a hydroxy group and/or where E and G together are CH$_2$ or CO, then A can also be a group of the formula

R$^2$ is lower-alkyl, aryl, heteroaryl or cycloalkyl optionally bonded via lower-alkylene, carbo-lower-alkoxy bonded via lower-alkylene or —(O or S)-(aryl, heteroaryl or cycloalkyl) bonded via lower-alkylene, whereby a lower-alkylene group present in R$^2$ can be substituted by hydroxy, amino or lower-alkanoylamino in the α-position to the carbonyl group to which R$^2$ is bonded or R$^2$ is halogen, carboxy, lower alkoxy, amino, mono- or di-lower-alkyl-amino or a group —N(Het) bonded via lower alkylene or R$^2$ is a group —OR$^{22}$ or —NHR$^{22}$, R$^{22}$ is lower-alkyl, or aryl, heteroaryl or cycloalkyl optionally bonded via lower-alkylene, or lower-aralkyl substituted in the lower-alkyl moiety by aryl, carbo-lower-alkoxy or COOH, R$^3$ and R$^4$ each independently are hydrogen, alkyl or aryl-lower-alkyl or together with the N atom to which they are attached form a group —N(Het), R$^5$ is aryl, heteroaryl, heterocyclyl, alkyl or cycloalkyl, —N(Het) is N-bonded —N(CH$_2$)$_{4-9}$ optionally interrupted by O, S, NH or N-lower-alkyl and optionally substituted by up to 2 substituents from the group of lower-alkyl, OH, oxo, COOH, COO-lower-alkyl, CH$_2$OH and CH$_2$O-benzyl, Q is a group of formula $Q^1$ or $Q^2$:

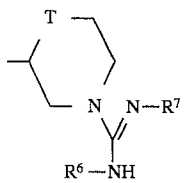
(Q¹)

and

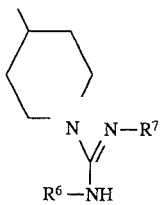
(Q²)

T is $CH_2$ or O, one of $R^6$ and $R^7$ is hydrogen or carbo-lower-alkoxy and the other is hydrogen, carbo-lower-alkoxy or hydroxy, and R is hydrogen or lower-alkyl, as well as hydrates or solvates and physiologically compatible salts thereof.

2. Carboxamides according to claim 1, wherein

E is hydrogen,

G is H, lower-alkyl or (optionally bonded via lower-alkylene) COOH, COO-lower-alkyl, lower-alkanoyl, OH, lower-alkanoyloxy, lower-alkoxy, aryl-lower-alkoxy, $CONH_2$, $CONHCH_2CH_2OH$, CONHOH, $CONHOCH_3$, CONHO-benzyl, $CONHSO_2$-lower-alkyl, $CONHCH_2CH_2$-aryl, CONH-cycloalkyl, $CONHCH_2$-heteroaryl, $NH_2$, NHCOO-lower-alkyl, NHCOO-lower-aralkyl, $NHSO_3H$, ($NHSO_2$ or $NHSO_3$)-lower-alkyl, NH lower-alkanoyl, NHCO-COOH, NHCOCOO-lower-alkyl, NH-cycloalkyl, NH-(3,4-dioxo-2-hydroxy-cyclobut-1-enyl), NH-[2-lower-(alkoxy or -alkenyloxy)-3,4-dioxocyclobut-1-enyl], $NHCH_2$-heteroaryl, NHCOCO-(aryl or lower-alkyl), $NHCOCH_2Cl$, $NHCOCH_2O$-aryl, $NHCOCH_2$-aryl, NHCO-(aryl or heteroaryl), $NHPO_3(R^{10},R^{20})$, heteroaryl or $CON(CH_2)_{4-9}$ optionally interrupted by O or S and optionally substituted by up to 2 substituents from the group of lower-alkyl, COOH, COO-lower-alkyl, $CH_2OH$ and $CH_2O$-benzyl, $R^{10}$ and $R^{20}$ are H, lower-alkyl or phenyl, M is H, lower-alkyl or -alkenyl, aryl, heteroaryl, cycloalkyl or (aryl, heteroaryl or cycloalkyl)-lower-alkyl and L is H, lower-alkyl, aryl, cycloalkyl, or (aryl or cycloalkyl)-lower-alkyl or M and L together with the atoms to which they are attached form a $N(CH_2)_{4-9}$ group which is optionally interrupted by O or S and optionally substituted by up to 2 substituents from the group of lower-alkyl, COOH, COO-lower-alkyl, $CH_2OH$, $CH_2O$-benzyl or E and G together form a methylene or carbonyl group and M is H, lower-alkyl or -alkenyl, aryl, heteroaryl, cycloalkyl, (aryl, heteroaryl or cycloalkyl)-lower-alkyl, or carboxy-lower-alkyl and L is H, lower-alkyl, aryl, cycloalkyl or (aryl or cycloalkyl)-lower-alkyl, A is a group of the formula:

—C(O)$R^2$ (A¹),

—S(O)$_2$N($R^3$,$R^4$) (A²)

or, where group Q contains a hydroxy group, A can also be a group of the formula

—S(O)$_2R^5$ (A³)

or where E and G together are $CH_2$ or CO,

A can also be H, alkyl or a group of the formula:

—S(O)$_2R^5$ (A³), $R^2$ is a group $R^{22}$, —$OR^{22}$ or —$NHR^{22}$ and $R^{22}$ is lower-alkyl or aryl, heteroaryl or cycloalkyl optionally bonded via lower-alkylene, or $R^2$ is carbo-lower-alkoxy bonded via lower-alkylene or —(O or S)-(aryl, heteroaryl or cycloalkyl) bonded via lower-alkylene, whereby a lower-alkylene group present in $R^2$ can be substituted by hydroxy, amino or lower-alkanoylamino in the α-position to the carbonyl group to which $R^2$ is bonded, $R^3$ and $R^4$ each independently are hydrogen, alkyl or aryl-lower-alkyl or together with the N atom to which they are attached are —$N(CH_2)_{4-9}$ which is optionally interrupted by O or S, $R^5$ is aryl, heteroaryl, heterocyclyl, alkyl or cycloalkyl, Q is a group of formula $Q^1$ or $Q^2$:

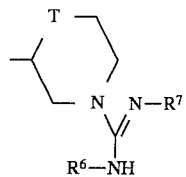
(Q¹)

and

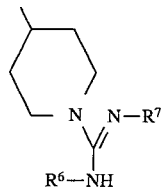
(Q²)

T is $CH_2$ or O, one of $R^6$ and $R^7$ is hydrogen or carbo-lower-alkoxy and the other is hydrogen, carbo-lower-alkoxy or hydroxy and R is hydrogen, as well as hydrates or solvates and physiologically compatible salts thereof.

3. Carboxamides according to claim 1 and of the formula

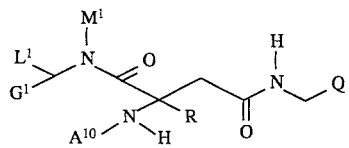
Ia wherein $G^1$ is H, lower-alkyl or (optionally bonded via lower-alkylene) COOH, COO-lower-alkyl, lower-alkanoyl, OH, lower-alkanoyloxy, lower-alkoxy, aryl-lower-alkoxy, $CONH_2$, $CONHCH_2CH_2OH$, CONHOH, $CONHOCH_3$, CONHO-benzyl, $CONHSO_2$-lower-alkyl, $CONHCH_2CH_2$-aryl, CONH-cycloalkyl, CON- HCH$_2$-heteroaryl, NH$_2$, NHCOO-lower-alkyl, NHCOO-lower-aralkyl, NHSO$_3$H, (NHSO$_2$ or NHSO$_3$)-lower-alkyl, NH-lower-alkanoyl, NHCO-COOH, NHCOCOO-lower-alkyl, NH-cycloalkyl, NH-(3,4-dioxo-2-hydroxy-cyclobut-1-enyl), NH-[2-lower-(alkoxy or -alkenyloxy)-3,4-dioxocyclobut-1-enyl], NHCH$_2$-heteroaryl, NHCOCO-(aryl or lower-alkyl), NHCOCH$_2$Cl, NHCO-lower-alkylene-O-(lower-alkyl or aryl), NHCOCH$_2$[aryl, heteroaryl or —N(Het)], NHCOC(NOH)-lower-alkylene-COOH, NHSO$_2$-N(Het), NHCO-(aryl, heteroaryl or heterocyclyl), NHPO$_3$(R$^{10}$,R$^{20}$), heteroaryl or a group CO—N(Het), R$^{10}$ and R$^{20}$ are H, lower-alkyl or phenyl, M$^1$ is H, lower-alkyl or -alkenyl, aryl, heteroaryl, cycloalkyl or (aryl, heteroaryl or cycloalkyl)-lower-alkyl and L$^1$ is H, lower-alkyl, aryl, cycloalkyl or (aryl or cycloalkyl)-lower-alkyl or M$^1$ and L$^1$ together with the atoms to which they are attached form a group —N(Het), A$^{10}$ is H, alkyl, lower-aralkyl or a group of the formula:

or, where group Q contains a hydroxy group, then A$^{10}$ can also be a group of the formula

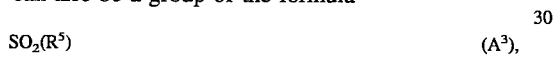

and

R, R$^2$ to R$^5$, —N(Het) and Q have the same significance as in claim 1, as well as hydrates or solvates and physiologically compatible salts thereof.

4. Carboxamides according to claim 1 and of the formula

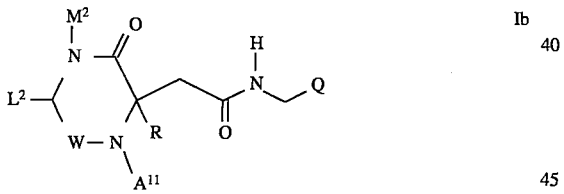

wherein

W is methylene or carbonyl,

M$^2$ is H, lower-alkyl or-alkenyl, aryl, heteroaryl, cycloalkyl, (aryl, heteroaryl or cycloalkyl)-lower-alkyl or carboxy-lower-alkyl, L$^2$ is H, lower-alkyl, aryl, cycloalkyl or (aryl or cycloalkyl)-lower-alkyl and A$^{11}$ is H, alkyl, lower-aralkyl or a group of the formula:

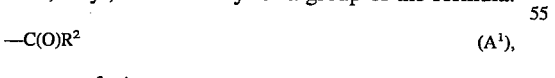

or

and

R, R$^2$ to R$^5$ and Q have the same significance as in claim 1, as well as hydrates or solvates and physiologically compatible salts thereof.

5. Carboxamides according to claim 3, wherein

G$^1$ is H, lower-alkyl or (optionally bonded via lower alkylene) COOH, COO-lower-alkyl, lower-alkanoyl, OH, lower-alkanoyloxy, lower-alkoxy, aryl-lower-alkoxy, CONH$_2$, CONHCH$_2$CH$_2$OH, CONHOH, CONHOCH$_3$, CONHO-benzyl, CONHSO$_2$-lower-alkyl, CONHCH$_2$CH$_2$-aryl, CONH-cycloalkyl, CONHCH$_2$-heteroaryl, NH$_2$, NHCOO-lower-alkyl, NHCOO-lower-aralkyl, NHSO$_3$H, (NHSO$_2$ or NHSO$_3$)-lower-alkyl, NH-lower-alkanoyl, NHCO-COOH, NHCOCOO-lower-alkyl, NH-cycloalkyl, NH-(3,4-dioxo-2-hydroxy-cyclobut-1-enyl), NH-[2-lower-(alkoxy or -alkenyloxy)-3,4-dioxocyclobut-1-enyl], NHCH$_2$-heteroaryl, NHCOCO-(aryl or lower-alkyl), NHCOCH$_2$Cl, NHCOCH$_2$O-aryl, NHCOCH$_2$-aryl, NHCO-(aryl or heteroaryl), NHPO$_3$(R$^{10}$,R$^{20}$), heteroaryl or CON(CH$_2$)$_{4-9}$ optionally interrupted by O or S and optionally substituted by up to 2 substituents from the group of lower-alkyl, COOH, COO-lower-alkyl, CH$_2$OH and CH$_2$O-benzyl, R$^{10}$ and R$^{20}$ are H, lower-alkyl or phenyl, M$^1$ is H, lower-alkyl or -alkenyl, aryl, heteroaryl, cycloalkyl or (aryl, heteroaryl or cycloalkyl)-lower-alkyl and L$^1$ is H, lower-alkyl, aryl, cycloalkyl or (aryl or cycloalkyl)-lower-alkyl or M$^1$ and L$^1$ together with the atoms to which they are attached form a N(CH$_2$)$_{4-9}$ group optionally interrupted by O or S and optionally substituted by up to 2 substituents from the group of lower-alkyl, COOH, COO-lower-alkyl, CH$_2$OH and CH$_2$O-benzyl, A$^{10}$ is a group of the formula

or, where group Q contains a hydroxy group, A$^{10}$ can also be a group of the formula

R is hydrogen and

R$^2$ to R$^5$ and Q have the same significance as in claim 3, as well as hydrates or solvates and physiologically compatible salts thereof.

6. Carboxamides according to claim 4, wherein

R is hydrogen,

A$^{11}$ is H, alkyl or a group of the formula:

or

and L$^2$, M$^2$, W, R$^2$ to R$^5$ and Q have the same significance as in claim 4, as well as hydrates or solvates and physiologically compatible salts thereof.

7. Carboxamides of formula Ia according to claim 3, wherein L$^1$ is hydrogen and G$^1$ is (optionally bonded via lower-alkylene) NHCO-lower-alkylene-O-(lower-alkyl or aryl), NHCOCH$_2$[aryl, heteroaryl or —N(Het)], NHCOC-(NOH)-lower-alkylene-COOH, NHSO$_2$-N(Het), NHCO-heterocyclyl or CON(CH$_2$)$_{4-9}$ optionally interrupted by O or S and optionally substituted by up to 2 substituents from the group of lower-alkyl, COOH, COO-lower-alkyl, CH$_2$OH and CH$_2$O-benzyl.

8. Carboxamides of formula Ia according to claim 3, wherein L$^1$ is hydrogen and G$^1$ is COOH, COO-lower-alkyl, NHCOO-lower-aralkyl or NHCO(aryl or heteroaryl) optionally bonded via lower-alkylene.

9. Carboxamides of formula Ia according to claim 3, 7 or 8, wherein M$^1$ is lower-alkyl or cycloalkyl.

10. Carboxamides of formula Ia according to claim 3 or any one of claims 7–9, wherein A$^{10}$ is H, lower-alkyl, lower-aralkyl or a group

—C(O)—R$^2$  (A$^1$)

in which R$^2$ is halogen, carboxy, lower-alkoxy, amino or mono- or di-lower-alkyl-amino bonded via lower-alkylene or a group —N(Het) bonded via lower-alkylene or R$^2$ is a group —NHR$^{22}$ in which R$^{22}$ is a lower-aralkyl group substituted in the lower-alkyl moiety by aryl, carbo-lower-alkoxy or COOH.

11. Carboxamides of formula Ia according to claim 3 or any one of claims 7–10, wherein A$^{10}$ is a group of the formula

—C(O)—R$^2$  (A$^1$)

in which R$^2$ is a group R$^{22}$, —OR$^{22}$ or —NHR$^{22}$ and R$^{22}$ is lower-alkyl or aryl, heteroaryl or cycloalkyl optionally bonded via lower-alkylene or in which R$^2$ is carbo-lower-alkoxy bonded via lower-alkylene or —(O or S)-(aryl or heteroaryl) bonded via lower-alkylene, whereby a lower-alkylene group present in R$^2$ can be substituted by OH or lower-alkanoylamino in the α-position to the carbonyl group to which R$^2$ is bonded.

12. Carboxamides of formula Ia according to claim 3, 8 or 9, wherein A$^{10}$ is morpholinosulphonyl.

13. Carboxamides of formula Ia according to claim 3, 8 or 9, wherein A$^{10}$ contains a group —S(O)$_2$aryl and Q contains a hydroxy group.

14. Carboxamides of formula Ib according to claim 4, wherein L$^2$ is hydrogen and M$^2$ is lower-alkyl, cycloalkyl or carboxy-lower-alkyl.

15. Carboxamides of formula Ib according to claim 4 or 14, wherein A$^{11}$ is hydrogen, lower-alkylsulphonyl or arylsulphonyl.

16. Carboxamides according to any one of claims 1–15, wherein Q is a group of formula Q$^1$ in which one of R$^6$ and R$^7$ is hydrogen and the other is hydrogen or hydroxy.

17. A compound of claim 3 which has the formula

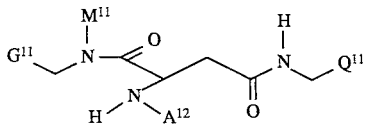

Ia1 wherein
G$^{11}$ is a group COOH, COO-lower-alkyl or NHCO-heteroaryl, which group is optionally bonded via lower-alkylene,
M$^{11}$ is lower-alkyl or cycloalkyl,
A$^{12}$ is lower-aralkyl or a group —C(O)R$^{21}$, —S(O)$_2$-aryl or —S(O)$_2$—N(Het),
R$^{21}$ is a group —S-heteroaryl or —N(Het)", which group is bonded via lower-alkylene, or R$^{21}$ is lower-aralkoxy or lower-alkyl,
—N(Het)" is N-bonded —N(CH$_2$)$_{4-9}$ optionally interrupted by O, S, NH or N-lower-alkyl, Q$^{11}$ is a group of formula

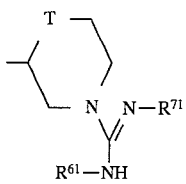

T is CH$_2$ or O,
one of R$^{61}$ and R$^{71}$ is H and the other is H or OH,
and physiologically compatible salts thereof.

18. The compound of claim 17, wherein G$^{11}$ is COOH optionally bonded via lower-alkylene.

19. The compound of claim 18, wherein M$^{11}$ is lower-alkyl.

20. The compound of claim 19, wherein A$^{12}$ is C(O)R$^{21}$.

21. The compound of claim 20, wherein R$^{21}$ is lower-aralkoxy.

22. The compound of claim 21, wherein T is O.

23. The compound of claim 22, wherein each R$^{61}$ and R$^{71}$ are H.

24. The compound of claim 23, i.e. [[(S)-3-[4-(amino-imino-methyl)-morpholin-2-ylmethylcarbamoyl]-2-benzyloxycarbonylaminopropionyl]-butyl-amino]-acetic acid.

25. The compound of claim 18, wherein M$^{11}$ is cycloalkyl.

26. The compound of claim 25, wherein A$^{12}$ is C(O)R$^{21}$.

27. The compound of claim 26, wherein R$^{21}$ is lower-alkyl.

28. The compound of claim 27, wherein T is CH$_2$.

29. The compound of claim 28, wherein each R$^{61}$ and R$^{71}$ are H.

30. The compound of claim 29, i.e. [[(S)-3-[(S)-1-(amino-imino-methyl)-piperidin-3-yl-methylcarbamoyl]-2-pentanoylaminopropionyl]-cyclopropyl-amino]-acetic acid.

31. The compound of claim 17, wherein G$^{11}$ is NHCO-heteroaryl optionally bonded via lower-alkylene.

32. The compound of claim 31, wherein M$^{11}$ is cycloalkyl.

33. The compound of claim 32, wherein A$^{12}$ is C(O)R$^{21}$.

34. The compound of claim 33, wherein R$^{21}$ is -S-heteroaryl bonded via lower-alkylene.

35. The compound of claim 34, wherein T is CH$_2$.

36. The compound of claim 35, wherein each R$^{61}$ and R$^{71}$ are H.

37. The compound of claim 36, i.e. (S)-N4-[(S)-1-(amino-imino-methyl)-piperidin-3-ylmethyl]-N1-cyclopropyl-N1-(2-pyrazin-2-ylcarbonylamino-ethyl)-2-pyrimidin-2-ylsulphanylacetylamino-succinamide.

38. The compound of claim 31 or 32, wherein A$^{12}$ is S(O)$_2$-aryl.

39. The compound of claim 38, wherein T is CH$_2$.

40. The compound of claim 39, wherein R$^{61}$ is H and R$^{71}$ is OH.

41. The compound of claim 40, i.e. (S)-N4-[(S)-1-(amino-hydroxyimino-methyl)-piperidin-3-ylmethyl]-N1-cyclopropyl-2-napthalen- 2-ylsulphonylamino)-N1-[2-(pyrazin-2-ylcarbonylamino)ethyl]-succinamide.

42. The compound of claim 31 or 32, wherein A$^{12}$ is S(O)$_2$-N(Het)".

43. The compound of claim 42, wherein T is CH$_2$.

44. The compound of claim 43, wherein each R$^{61}$ and R$^{71}$ are H.

45. The compound of claim 44, i.e. (S)-N4-[(S)-1-(amino-imino-methyl)-piperidin-3-ylmethyl]-N1-cyclopropyl-2-morpholin-4-ylsulphonylamino-N1-[2-(6-oxo-1,6-dihydro-pyridazin-3-ylcarbonylamino-ethyl]-succinamide.

46. The compound of claim 31 or 32, wherein $A^{12}$ is $C(O)R^{21}$.

47. The compound of claim 46, wherein $R^{21}$ is N(Het)" bonded via lower-alkylene.

48. The compound of claim 47, wherein T is $CH_2$.

49. The compound of claim 48, wherein each $R^{61}$ and $R^{71}$ are H.

50. The compound of claim 49, i.e. (S)-N4-[(S)-1-(amino-imino-methyl)-piperidin-3-ylmethyl]-N1-cyclopropyl-2-morpholin-4-ylacetylamino-N1-(2-pyrazin-2-ylcarbonylamino-ethyl)-succinamide.

51. The compound of claim 17, wherein $G^{11}$ is COO-lower-alkyl optionally bonded via lower-alkylene.

52. The compound of claim 51, wherein $M^{11}$ is cycloalkyl.

53. The compound of claim 52, wherein $A^{12}$ is lower-aralkyl.

54. The compound of claim 53, wherein T is $CH_2$.

55. The compound of claim 54, wherein each $R^{61}$ and $R^{71}$ are H.

56. The compound of claim 55, i.e. ethyl 3-[[(S)-3-[(S)-1-(amino-imino-methyl)-piperidin-3-ylmethylcarbamoyl]-2-(3-phenylpropylamino)propionyl]-cyclopropyl-amino]-propionate.

57. The compound of claim 17, wherein $M^{11}$ is cycloalkyl.

58. The compound of claim 57, wherein $A^{12}$ is lower-aralkyl.

59. The compound of claim 58, wherein T is $CH_2$.

60. The compound of claim 59, wherein each $R^{61}$ and $R^{71}$ are H.

61. The compound of claim 60, i.e. 3-[[(S)-3-[(S)-1-(amino-imino-methyl)-piperidin-3-ylmethylcarbamoyl]-2-(3-phenylpropylamino)propionyl]-cyclopropyl-amino]-propionic acid.

62. The compound of claim 57, wherein $A^{12}$ is $S(O)_2$-N(Het)".

63. The compound of claim 62, wherein T is $CH_2$.

64. The compound of claim 63, wherein $R^{61}$ and $R^{71}$ are H.

65. The compound of claim 64, i.e. 3-[[(S)-3-[(S)-1-(amino-imino-methyl)-piperidin-3-yl-methylcarbamoyl]-2-morpholin-4-ylsulphonylamino-propionyl]-cyclopropyl-amino]-propionic acid.

66. A compound of claim 4, wherein W is carbonyl.

67. The compound of claim 66, wherein $M^2$ is cycloalkyl.

68. The compound of claim 67, wherein $L^2$ is H.

69. The compound of claim 68, wherein $A^{11}$ is $-S(O)_2R^5$.

70. The compound of claim 69, wherein $R^5$ is aryl.

71. The compound of claim 70, wherein R is H.

72. The compound of claim 71, wherein Q is $Q^1$, T is $CH_2$, and each $R^6$ and $R^7$ are H.

73. The compound of claim 72, i.e. N-[(S)-1-(amino-imino-methyl)-piperidin-3-ylmethyl]-2-[(S)-4-cyclopropyl-1-naphthalen-2-ylsulphonyl-3,6-dioxo-piperazin-2-yl]-acetamide.

74. The compound of claim 16 wherein said compound is 3-[[(S)-3-[(S)-1-(amino-imino-methyl)-piperidin-3-ylmethylcarbamoyl]-2-butylamino-propionyl]-cyclopropyl-amino]-propionic acid hydrochloride.

* * * * *

UNITED STATES PATENT AND TRADEMARK OFFICE
CERTIFICATE OF CORRECTION

PATENT NO. : 5,559,232
DATED : September 24, 1994
INVENTOR(S) : Jean Ackermann et al.

It is certified that error appears in the above-indentified patent and that said Letters Patent is hereby corrected as shown below:

In claim 2 at Column 38, Line 51, the sixth word "solyates" should read --solvates--.

Signed and Sealed this

Twenty-fourth Day of December, 1996

Attest:

BRUCE LEHMAN

*Attesting Officer*  *Commissioner of Patents and Trademarks*